US012655351B2

(12) United States Patent
Okabe et al.

(10) Patent No.: US 12,655,351 B2
(45) Date of Patent: Jun. 16, 2026

(54) LIQUID CRYSTALLINE COMPOUND, LIQUID CRYSTAL COMPOSITION, AND ELEMENT

(71) Applicants: JNC CORPORATION, Tokyo (JP); JNC PETROCHEMICAL CORPORATION, Tokyo (JP)

(72) Inventors: Eiji Okabe, Chiba (JP); Takanori Mori, Chiba (JP); Kazushi Shiren, Chiba (JP); Yuko Katano, Chiba (JP); Yujiro Oguchi, Chiba (JP); Kosuke Mine, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 19/289,125

(22) Filed: Aug. 4, 2025

(65) Prior Publication Data

US 2026/0159758 A1 Jun. 11, 2026

(30) Foreign Application Priority Data

Dec. 6, 2024 (JP) ................................ 2024-212994
Jun. 12, 2025 (JP) ................................ 2025-098187

(51) Int. Cl.

| | |
|---|---|
| *G02F 1/1333* | (2006.01) |
| *C07C 331/28* | (2006.01) |
| *C09K 19/30* | (2006.01) |
| *G02B 30/28* | (2020.01) |

(52) U.S. Cl.

CPC ........ *C09K 19/3059* (2013.01); *C07C 331/28* (2013.01); *C09K 19/3001* (2013.01); *G02B 30/28* (2020.01); *C07B 2200/13* (2013.01); *C07C 2601/14* (2017.05); *C09K 2019/3065* (2013.01)

(58) Field of Classification Search

CPC .............. C07C 331/28; C09K 19/3001; C09K 19/3059; C09K 2019/3065; G02F 1/1333

See application file for complete search history.

(56) References Cited

U.S. PATENT DOCUMENTS 12,252,643 B2 * 3/2025 Okabe ................ C09K 19/3059

FOREIGN PATENT DOCUMENTS

| | | | |
|---|---|---|---|
| CN | 116332800 A * | 6/2023 | ............ C09K 19/18 |
| JP | 2004285085 | 10/2004 | |
| JP | 2011074074 | 4/2011 | |
| WO | 2017201515 | 11/2017 | |
| WO | 2017208996 | 12/2017 | |

OTHER PUBLICATIONS

Machine translation of CN-116332800-A (Year: 2023).*

Hiroshi Moritake, "Microwave / millimeter wave phase control device (1st) Microwave characteristics of liquid crystal display," Ekisho, vol. 23, Jan. 2019, with partial English translation thereof, pp. 1-7.

Yoshio Inuishi, "Dielectric Phenomenon Theory," Institute of Electrical Engineers of Japan, Ohmsha, Ltd., Jul. 1973, with partial English translation thereof, pp. 1-9.

* cited by examiner

*Primary Examiner* — Geraldina Visconti

(74) *Attorney, Agent, or Firm* — JCIPRNET

(57) ABSTRACT

A compound is represented by Formula (1).

(1)

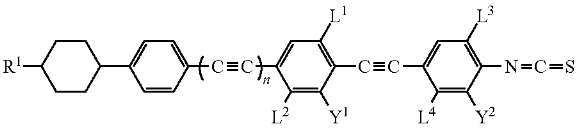

For example, $R^1$ is alkyl having 1 to 12 carbon atoms; $L^1$ is fluorine; $L^2$ is hydrogen; $L^3$ is fluorine; $L^4$ is methyl; $Y^1$ is hydrogen; $Y^2$ is hydrogen; and n is 0.

20 Claims, No Drawings

LIQUID CRYSTALLINE COMPOUND, LIQUID CRYSTAL COMPOSITION, AND ELEMENT

CROSS-REFERENCE TO RELATED APPLICATION

This application claims the priority benefit of Japan application serial no. 2024-212994, filed on Dec. 6, 2024 and Japan application serial no. 2025-098187, filed on Jun. 12, 2025. The entirety of the above-mentioned patent applications is hereby incorporated by reference herein and made a part of this specification.

BACKGROUND

Technical Field

The disclosure relates to a liquid crystalline compound, a liquid crystal composition having a nematic phase and a positive dielectric anisotropy, and an element including the same. The disclosure particularly relates to a liquid crystal composition used for electromagnetic wave control in a frequency range from 1 GHz to 10 THz, and an element including the same.

Related Art

As a new use of liquid crystal compositions widely used for displays, application of liquid crystal compositions to high-frequency technology such as antennas for transmitting and receiving electromagnetic waves has been attracting attention.

Specific examples of elements used for electromagnetic wave control in a frequency range from 1 GHz to 10 THz include millimeter-wave band or microwave band antenna arrays and electromagnetic wave reflectors. Various systems have been examined for these elements, and a system using a liquid crystal composition, which is thought to be less likely to fail because it has no mechanically movable parts, has been attracting attention.

In communication technology, high-frequency bands have not been widely utilized so far. However, due to demands for an ultra-high-speed large capacity, a low latency, multiple simultaneous connections, etc., the utilization of the millimeter-wave band (24 GHz to 100 GHz) in particular can be expected. For such a use, allocation of frequency bands has begun worldwide. As the millimeter-wave frequencies used in communication, 24 to 29.5 GHz has been allocated in about 20 countries, and in the United States, the range has expanded to 37 to 40 GHz and 47.2 to 48.2 GHz. In the future, higher frequencies may be allocated in many countries. In Japan, 27 to 29.5 GHz has been allocated to mobile phone operators for commercial use. In this manner, the use of millimeter waves centered on frequency bands around 28 GHz is increasing in many countries.

A liquid crystal composition having dielectric anisotropy has different dielectric constants in vertical and horizontal directions with respect to an orientation direction of the liquid crystal composition at frequencies (from about several tens of kHz to several hundreds of MHz) lower than a frequency (relaxation frequency) at which orientational polarization is relaxed.

Even at frequencies higher than the relaxation frequency, that is, in a range from microwaves to terahertz waves (approximately 10 THz), a difference in the dielectric constant between the vertical direction and the horizontal direction with respect to the orientation direction of the liquid crystal composition is observed, although the value is small. Thus, the liquid crystal composition has dielectric anisotropy (Non-Patent Document 1: EKISHO, Vol. 23 (No. 1), (2019), pp. 51-55). For this reason, in the liquid crystal composition, an orientation direction of molecules can be changed in response to an external field (electric field) to change the dielectric constant in one direction.

By utilizing this property, the liquid crystal composition is capable of changing orientation of molecules in response to an external electric field to change the dielectric constant. For example, it is possible to realize a microwave device that can electrically control transmission properties of a high-frequency transmission line from outside. As such devices, a voltage-controlled millimeter-wave band variable phase shifter in which a waveguide is filled with a nematic liquid crystal composition, a microwave/millimeter-wave band wideband variable phase shifter in which a nematic liquid crystal composition is used as a dielectric substrate for a microstrip line, etc. have been reported (Patent Document 1 (PCT International Publication No. WO 2017/201515) and Patent Document 2 (PCT International Publication No. WO 2017/208996)).

In addition, in recent years, research on metamaterial technology, which exhibits behavior that is not found in natural substances against electromagnetic waves including light, has been progressing. Due to such a property, the technology is applied to technical fields such as high-frequency devices, microwave devices, and antennas, and various electromagnetic wave control elements have been devised. As a capacitance control material for a transmission line using a metamaterial, use of a liquid crystal composition capable of changing orientation of molecules in response to an external electric field to change the dielectric constant has also been considered.

Elements used for such electromagnetic wave control desirably have properties such as a high gain and a low loss. Considering phase control of high-frequency signals, the properties required for a liquid crystal composition are: a large dielectric anisotropy that enables large phase control in a frequency domain used for phase control; and a small dielectric loss tangent (tan δ) proportional to absorption energy of electromagnetic wave signals of the liquid crystal composition (Non-Patent Document 1).

Since a liquid crystal composition is a dielectric, it causes polarization (dielectric polarization) with respect to an external field (electric field). A dielectric constant is a physical quantity that indicates a response of the dielectric with respect to an electric field, and the magnitude of the dielectric constant is related to dielectric polarization. The mechanism by which dielectric polarization occurs is roughly divided into three, including electronic polarization, ionic polarization, and orientational polarization. Orientational polarization is polarization associated with orientation of a dipole moment, and as shown above, it relaxes at frequencies from about several hundreds of kHz to several hundreds of MHz, and the orientational polarization becomes small. As a result, dielectric polarization at high frequencies (a range from microwaves to terahertz waves (approximately 10 THz)) involves only electronic polarization and ionic polarization. In a lossless dielectric, the relationship between a dielectric constant and a refractive index is $8=n^2$. If ionic polarization of a liquid crystal composition is considered to be small, it is thought that the larger the refractive index anisotropy (Δn) in visible light caused by electronic polarization, the larger the dielectric anisotropy (As) in a high-frequency domain (Non-Patent Document 2: Dielectric Phenomenon Theory, The Institute of Electrical Engineers of Japan, Ohmsha Ltd., Jul. 25, 1973, pp. 92-95). For this reason, a liquid crystal composition preferably has a large refractive index anisotropy.

In addition, a low driving voltage is desirable to realize switching properties and high energy efficiency of the elements. For this reason, a liquid crystal composition preferably has a large dielectric anisotropy even at low frequencies (frequencies lower than the relaxation frequency).

In addition, elements used for electromagnetic wave control are required to have a wide operating temperature range, a short response time of element, etc. Liquid crystal compositions are also required to have properties such as a high upper limit temperature of a nematic phase, a low lower limit temperature of a nematic phase, stability against heat, and a small viscosity.

Liquid crystal compositions used in the conventional elements are disclosed in Patent Document 3 (Japanese Patent Application Laid-Open Publication No. 2004-285085) and Patent Document 4 (Japanese Patent Application Laid-Open Publication No. 2011-74074).

As materials for elements used for electromagnetic wave control, liquid crystal compositions are required to: have a high upper limit temperature of a nematic phase and a low lower limit temperature of a nematic phase, have a large dielectric anisotropy (large refractive index anisotropy) and a small dielectric loss tangent (tan δ) in the frequency domain for electromagnetic wave control and a large dielectric anisotropy at low frequencies for reducing the driving voltage, and more preferably have a small viscosity, a high specific resistance in the driving frequency domain, and stability against heat.

However, the conventional liquid crystal compositions used for display have poor properties as such liquid crystal compositions used in elements used for electromagnetic wave control. This is because they have properties, such as a high insertion loss and/or a poor phase shift, which are poor for the use in high-frequency control.

Liquid crystal materials for elements used for electromagnetic wave control are still developing. To improve properties for high-frequency control, constant attempts have been made to develop novel compounds that enable optimization of such elements. A unique liquid crystal composition is required for use as a material for elements used for electromagnetic wave control.

SUMMARY

As a result of intensive studies, the inventors have found that a liquid crystal composition containing a liquid crystalline compound represented by Formula (1) having a specific structure addresses the above issue, thus completing the disclosure.

The disclosure includes the following items and the like.

Item 1. A compound represented by Formula (1), (1)

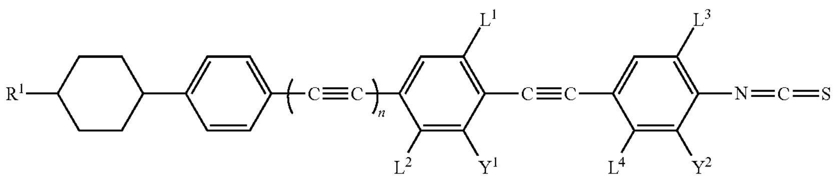

in Formula (1), $R^1$ is hydrogen, halogen, or alkyl having 1 to 12 carbon atoms, and in this alkyl, at least one $—CH_2—$ may be substituted with —O— or —S—, at least one $—(CH_2)_2—$ may be substituted with —CH═CH— or —C≡C—, and in these groups, at least one hydrogen may be substituted with halogen;

$L^1$, $L^2$, $L^3$, and $L^4$ are hydrogen, fluorine, chlorine, methyl, or ethyl;

$Y^1$ and $Y^2$ are hydrogen, fluorine, or chlorine; and n is 0 or 1.

With n being 0, a case where any two of $L^1$, $L^2$, $L^3$, and $L^4$ are methyl and the remaining two are hydrogen, fluorine, chlorine, or ethyl does not exist.

Item 2. The compound according to item 1, in which the compound represented by Formula (1) is represented by any one of Formula (1-1) to Formula (1-18), (1-1)

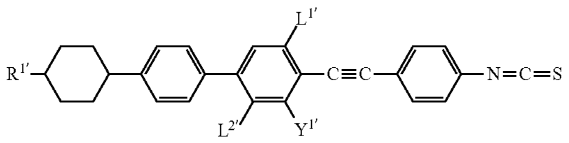

(1-2)

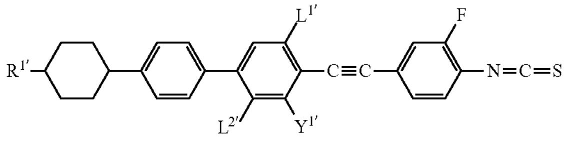

(1-3)

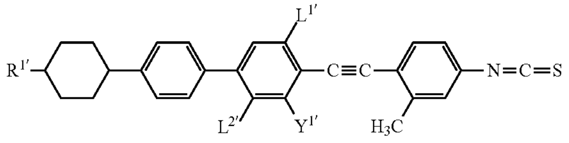

(1-4)

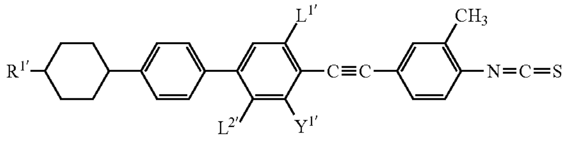

(1-5)

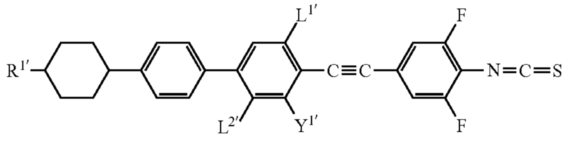

-continued (1-6)

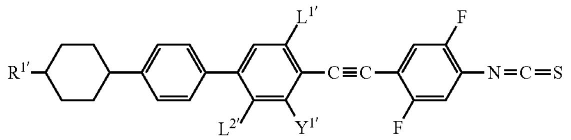

(1-7)

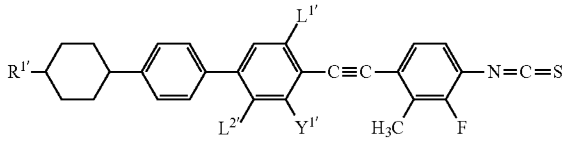

(1-8)

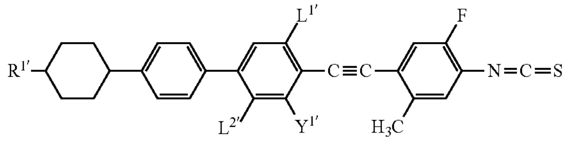

(1-9)

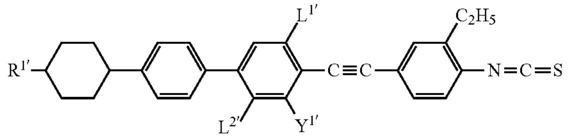

(1-10)

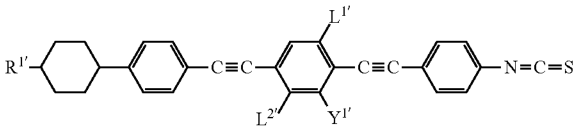

(1-11)

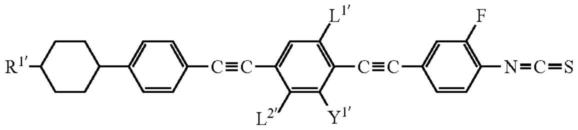

(1-12)

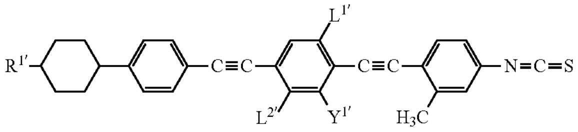

(1-13)

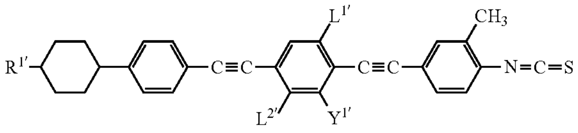

(1-14)

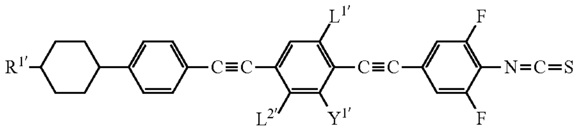

-continued (1-15)

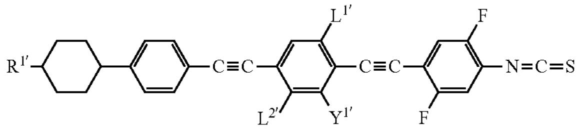

(1-16)

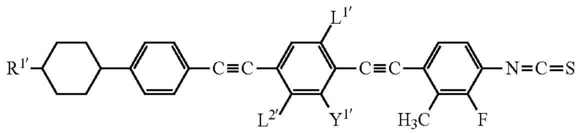

(1-17)

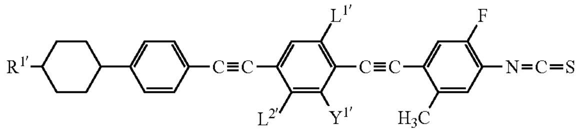

(1-18)

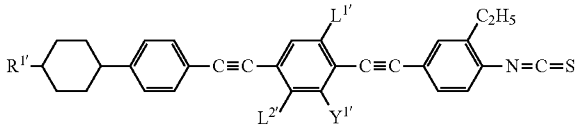

in Formula (1-1) to Formula (1-18), $R^{1'}$ is alkyl having 1 to 12 carbon atoms, and in this alkyl, at least one $—CH_2—$ may be substituted with —O— or —S—, at least one $—(CH_2)_2—$ may be substituted with —CH═CH— or —C≡C—, and in these groups, at least one hydrogen may be substituted with halogen;

$L^{1'}$ is fluorine or methyl, and $L^{2'}$ is hydrogen, fluorine, or methyl; and $Y^{1'}$ is hydrogen or fluorine.

In Formula (1-1), Formula (1-2), Formula (1-5), Formula (1-6), and Formula (1-9), a case where $L^{1'}$ and $L^{2'}$ are simultaneously methyl does not exist; and in Formula (1-3), Formula (1-4), Formula (1-7), and Formula (1-8), a case where only one of $L^{1'}$ and $L^{2'}$ is methyl does not exist.

Item 3. A liquid crystal composition containing at least one of the compound according to item 1 or 2.

Item 4. The liquid crystal composition according to item 3, further containing at least one compound selected from compounds represented by Formula (2) and Formula (3), (2)

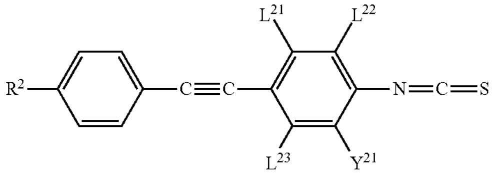

(3)

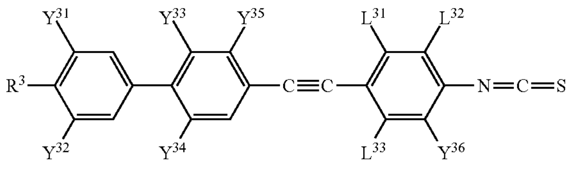

in Formula (2) and Formula (3), $R^2$ and $R^3$ are hydrogen, halogen, or linear alkyl having 1 to 12 carbon atoms, and in this alkyl, at least one $—CH_2—$ may be substituted with —O— or —S—, at least one $—(CH_2)_2—$ may be substituted with —CH═CH— or —C≡C—, and in these groups, at least one hydrogen may be substituted with halogen;

$L^{21}$, $L^{22}$, $L^{23}$, $L^{31}$, $L^{32}$, and $L^{33}$ are hydrogen, halogen, alkyl having 1 to 3 carbon atoms, fluorinated alkyl having 1 to 3 carbon atoms, or cycloalkyl having 3 to 5 carbon atoms; and $Y^{21}$, $Y^{31}$, $Y^{32}$, $Y^{33}$, $Y^{34}$, $Y^{35}$, and $Y^{36}$ are hydrogen or halogen.

Item 5. The liquid crystal composition according to item 3 or 4, containing at least one compound selected from the group of compounds represented by Formula (2-1) to Formula (2-10) as the compound represented by Formula (2), (2-1)

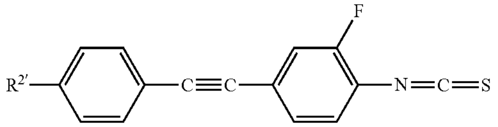

(2-2)

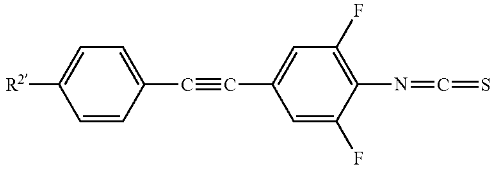

(2-3)

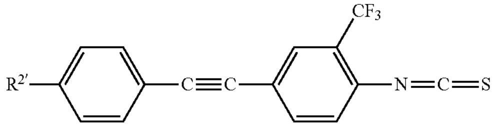

(2-4)

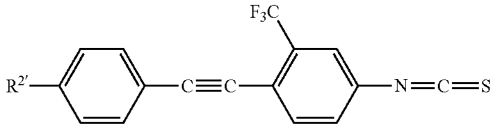

(2-5)

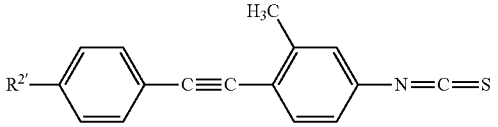

(2-6)

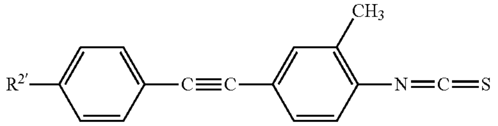

(2-7)

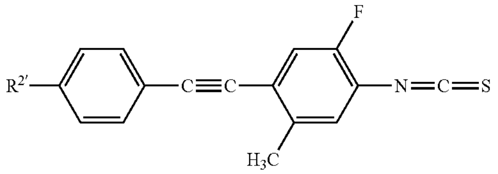

-continued (2-8)

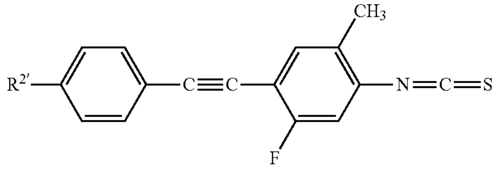

(2-9)

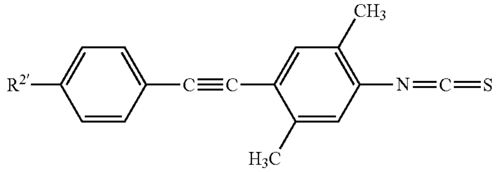

(2-10)

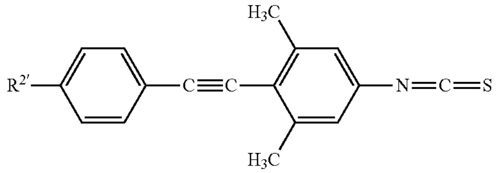

in Formula (2-1) to Formula (2-10), $R^{2'}$ is linear alkyl having 1 to 12 carbon atoms, and in this alkyl, at least one $—(CH_2)_2—$ may be substituted with —CH═CH— or —C≡C—.

Item 6. The liquid crystal composition according to any one of items 3 to 5, containing at least one compound selected from the group of compounds represented by Formula (3-1) to Formula (3-11) as the compound represented by Formula (3), (3-1)

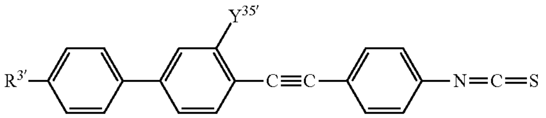

(3-2)

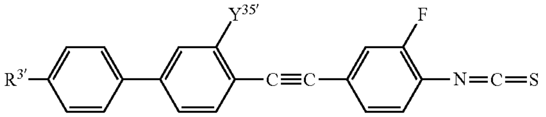

(3-3)

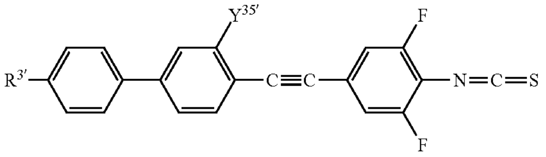

(3-4)

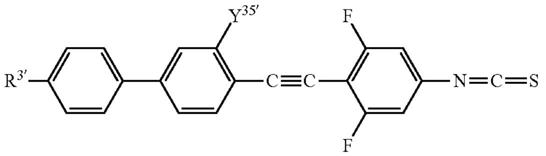

-continued (3-5)

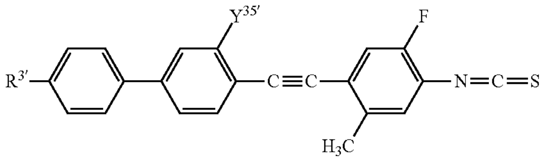

(3-6)

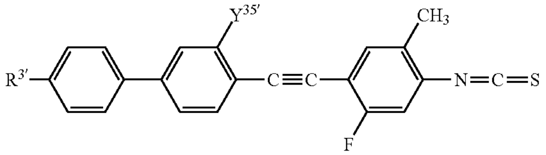

(3-7)

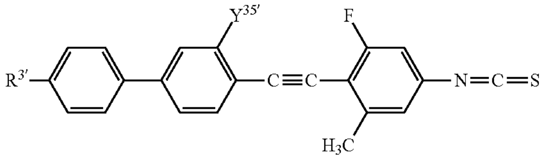

(3-8)

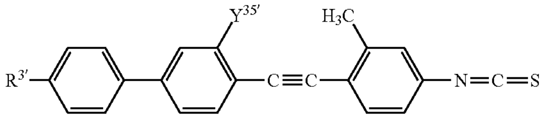

(3-9)

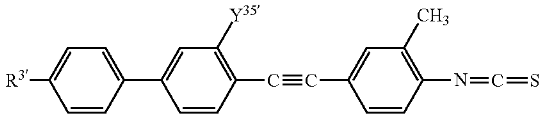

(3-10)

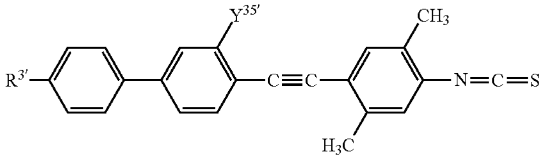

(3-11)

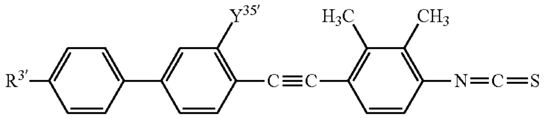

in Formula (3-1) to Formula (3-11), $R^{3'}$ is linear alkyl having 1 to 12 carbon atoms, and in this alkyl, at least one $-(CH_2)_2-$ may be substituted with $-CH{=}CH-$ or $-C{\equiv}C-$; and $Y^{35'}$ is hydrogen, fluorine, or chlorine.

Item 7. The liquid crystal composition according to any one of items 3 to 5, in which based on a weight of the liquid crystal composition, a proportion of the compound represented by Formula (1) according to item 1 is in a range from 5 weight % to 25 weight %, and a proportion of the compound represented by Formula (2) is in a range from 10 weight % to 55 weight %.

Item 8. The liquid crystal composition according to any one of items 3, 4, and 6, in which based on a weight of the liquid crystal composition, a proportion of the compound represented by Formula (1) according to item 1 is in a range from 5 weight % to 25 weight %, and a proportion of the compound represented by Formula (3) is in a range from 20 weight % to 50 weight %.

Item 9. The liquid crystal composition according to any one of items 3 to 6, in which based on a weight of the liquid crystal composition, a proportion of the compound represented by Formula (1) according to item 1 is in a range from 5 weight % to 25 weight %, a proportion of the compound represented by Formula (2) is in a range from 10 weight % to 55 weight %, and a proportion of the compound represented by Formula (3) is in a range from 20 weight % to 50 weight %.

Item 10. The liquid crystal composition according to any one of items 3 to 7, in which a refractive index anisotropy at 25° C. at a wavelength of 589 nm is 0.40 or more.

Item 11. The liquid crystal composition according to any one of items 3 to 8, in which a dielectric anisotropy at 25° C. at a frequency of 1 kHz is 10 or more.

Item 12. The liquid crystal composition according to any one of items 3 to 9, in which a dielectric anisotropy at 25° C. in at least one frequency range from 1 GHz to 10 THz is in a range from 1.0 to 3.0.

Item 13. The liquid crystal composition according to any one of items 3 to 10, containing an optically active compound.

Item 14. The liquid crystal composition according to any one of items 3 to 11, containing a polymerizable compound.

Item 15. The liquid crystal composition according to any one of items 3 to 12, further containing at least one of an antioxidant, an ultraviolet absorber, an antistatic agent, and a dichroic dye.

Item 16. An element including the liquid crystal composition according to any one of items 3 to 13, the element being used for switching and capable of reversibly controlling a dielectric constant by reversibly changing an orientation direction of liquid crystal molecules.

Item 17. An element including the liquid crystal composition according to any one of items 3 to 13 and used for electromagnetic wave control in a frequency range from 1 GHz to 10 THz.

Item 18. A liquid crystal lens, a birefringent lens for stereoscopic image display, or a light modulator, including the liquid crystal composition according to any one of items 3 to 13.

According to the disclosure, it is possible to provide a liquid crystalline compound that satisfies at least one of physical properties of the compound, such as stability against heat, a high clearing point, a very large refractive index anisotropy, and excellent compatibility with other liquid crystalline compounds. The composition containing the compound of the disclosure is capable of satisfying at least one of properties of the composition, such as a large dielectric anisotropy (large refractive index anisotropy) in a frequency domain for electromagnetic wave control, a small dielectric loss tangent (tan δ), and a large dielectric anisotropy at low frequencies for reduction of driving voltage, while having a high upper limit temperature of a nematic phase and a low lower limit temperature of the nematic phase. Furthermore, it is possible to further satisfy at least one of properties of the composition, such as a liquid crystal composition having a small viscosity, a large specific resistance in a driving frequency domain, and stability against heat. An element using this composition is capable of exhibiting excellent properties capable of controlling electromagnetic waves over a wide temperature range.

DESCRIPTION OF THE EMBODIMENTS

Embodiments of the disclosure provide a liquid crystalline compound and a liquid crystal composition which are well-balanced and excellent in required properties as a material used in elements for electromagnetic wave control in a frequency range from 1 GHz to 10 THz, and an element including this composition.

Terms used in this specification are as follows. The terms “liquid crystal composition” and “electromagnetic wave control element” are respectively sometimes abbreviated as “composition” and “element.” “Electromagnetic wave control element” is a general term for an electromagnetic wave control panel and an electromagnetic wave control module. “Liquid crystalline compound” is a general term for a compound having a liquid crystal phase such as a nematic phase or a smectic phase and a compound which does not have a liquid crystal phase but is mixed into a composition to adjust the properties such as dielectric anisotropy, a viscosity, and a temperature range of a liquid crystal phase. This compound has, for example, a 6-membered ring such as 1,4-cyclohexylene or 1,4-phenylene, and its molecules (liquid crystal molecules) are rod-like. “Polymerizable compound” is a compound added to form a polymer in a composition. A liquid crystalline compound having alkenyl is not classified as a polymerizable compound in that sense.

A liquid crystal composition is prepared by mixing multiple liquid crystalline compounds. The proportion (content) of the liquid crystalline compounds is represented by weight percentage (weight %) based on the weight of this liquid crystal composition. Additives such as an optically active compound, an antioxidant, an ultraviolet absorber, a stabilizer against ultraviolet rays or heat, a quencher, dyes (dichroic dyes), a defoamer, a polymerizable compound, a polymerization initiator, a polymerization inhibitor, an antistatic agent, and a magnetic compound are added to this liquid crystal composition as necessary. The proportion (addition amount) of the additives is represented by weight percentage (weight %) based on the weight of the liquid crystal composition similarly to the proportion of the liquid crystalline compounds. Parts per million (ppm) by weight are sometimes used. The proportions of a polymerization initiator and a polymerization inhibitor are exceptionally expressed based on the weight of the polymerizable compounds.

“Upper limit temperature of a nematic phase” is sometimes abbreviated as “upper limit temperature.” “Lower limit temperature of a nematic phase” is sometimes abbreviated as “lower limit temperature.” An expression “increasing dielectric anisotropy” means that the value increases positively in the case of a composition with a positive dielectric anisotropy, and means that the value increases negatively in the case of a composition with a negative dielectric anisotropy.

At least one compound selected from the group consisting of compounds represented by Formula (1) is sometimes abbreviated as “compound (1).” “Compound (1)” means one or more compounds represented by Formula (1). The same applies to compounds represented by other formulae. “At least one” relating to “may be substituted” means that not only a position but also the number thereof may be selected without limitation.

(1z)

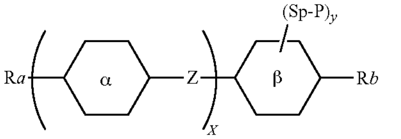

The above compound (1z) will be described as an example. In Formula (1z), the symbols α and β surrounded by hexagons correspond to a ring α and a ring β, respectively, and represent rings such as six-membered rings and condensed rings. When the subscript ‘x’ is 2, there are two rings α. Two groups represented by two rings α may be the same as or different from each other. This rule applies to multiple rings α when the subscript ‘x’ is greater than 2. This rule also applies to other symbols such as a bonding group Z. The slash across one side of the ring R indicates that any hydrogen on the ring R may be substituted with a substituent (—Sp—P). The subscript ‘y’ indicates the number of substituents substituted. When the subscript ‘y’ is 0, there is no such substitution. When the subscript ‘y’ is 2 or more, there are multiple substituents (—Sp—P) on the ring β. The rule that they “may be the same as or different from each other” also applies to this case. This rule also applies to a case where the symbol Ra is used for multiple compounds.

In Formula (1z), for example, an expression such as “Ra and Rb are alkyl, alkoxy, or alkenyl” means that Ra and Rb are independently selected from the group consisting of alkyl, alkoxy, and alkenyl. Herein, a group represented by Ra and a group represented by Rb may be the same as or different from each other. This rule also applies to a case where the symbol Ra is used for multiple compounds. This rule also applies to a case where multiple Ra’s are used for one compound.

At least one compound selected from compounds represented by Formula (1z) is sometimes abbreviated as “compound (1z).” “Compound (1z)” means one compound represented by Formula (1z), a mixture of two compounds thereof, or a mixture of three or more compounds thereof. The same applies to compounds represented by other formulae. An expression “at least one compound selected from compounds represented by Formula (1z) and Formula (2z)” means at least one compound selected from the group consisting of compounds (1z) and compounds (2z).

An expression “at least one ‘A’” means that the number of ‘A’s is any number. An expression “at least one ‘A’ may be substituted with ‘B’” means that the position of ‘A’ is any position when the number of ‘A’s is 1, and the positions of ‘A’s may be selected without limitation even when the number of ‘A’s is 2 or more. An expression “at least one $—CH_2—$ may be substituted with —O—” is sometimes used. In this case, $—CH_2—CH_2—CH_2—$ may be converted to $—O—CH_2—O—$ by substituting non-adjacent $—CH_2—$ with —O—. However, adjacent $—CH_2—$ is not substituted with —O—. This is because $—O—O—CH_2—$ (peroxide) would be produced by this substitution.

In the case of being simply described as “alkyl”, alkyl in a liquid crystalline compound is linear alkyl or branched alkyl and does not include cycloalkyl unless otherwise specified. For example, alkyl having 1 to 12 carbon atoms refers to linear alkyl or branched alkyl having 1 to 12 carbon atoms. Linear alkyl is preferable over branched alkyl. The same applies to terminal groups such as alkoxy and alkenyl. The configuration of 1,4-cyclohexylene is preferably trans rather than cis to increase the upper limit temperature. 2-fluoro-1,4-phenylene means two divalent groups below. In the chemical formulae, fluorine may be directed leftward (L) or rightward (R). This rule also applies to divalent groups of asymmetric rings such as 2,5-difluoro-1,4-phenylene, 2,6-difluoro-1,4-phenylene, pyridine-2,5-diyl, pyrimidine-2,5-diyl, 1,3-dioxane-2,5-diyl, and tetrahydropyran-2,5-diyl. Preferable tetrahydropyran-2,5-diyl is directed rightward (R) to increase the upper limit temperature.

(L)

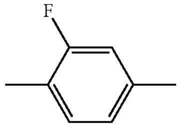

(R)

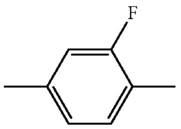

(L)

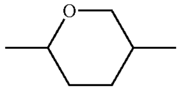

(R)

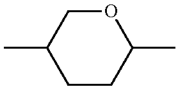

crystal composition may be suitably used not only in the range from 1 GHz to 10 THz, but also as an element related to electromagnetic waves (microwaves) in the range from 1 GHz to 50 GHz.

1. Compound (1)

A compound (1) of the disclosure will be described in the following order. In 1-1, preferable forms of the compound (1) will be described. In 1-2, preferable embodiments of the compound (1) will be shown. In 1-3, a synthesis method of the compound (1) will be described.

1-1. Forms of Compound (1)

The compound (1) of the disclosure will be described. Preferable examples of terminal groups, bonding groups, etc. in the compound (1), and the effects that these groups create on physical properties also apply to sub-formulae of the compound (1).

(1)

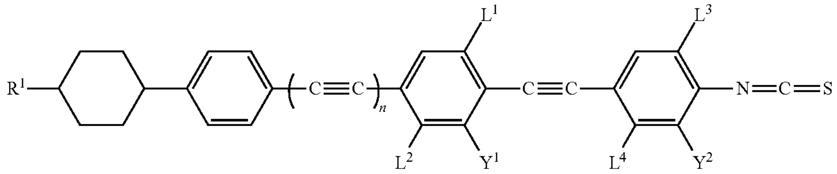

A bonding group such as carbonyloxy may similarly be —COO— or —OCO—.

In chemical formulae of component compounds, the symbol $R^1$ for a terminal group is used for multiple compounds. In these compounds, any two groups represented by $R^1$ may be the same as or different from each other. For example, there is a case where $R^{1'}$ of a compound (1-1) is methyl and $R^{1'}$ of a compound (1-2) is ethyl. There is also a case where $R^{1'}$ of the compound (1-1) is ethyl and $R^{1'}$ of the compound (1-2) is propyl. This rule also applies to symbols such as $R^2$, $R^3$, $R^4$, $R^5$, $R^6$, $R^{71}$, and $R^{72}$.

The disclosure also includes the following items. (a) The above-described composition further containing at least one selected from additives such as an optically active compound, an antioxidant, an ultraviolet absorber, a stabilizer against ultraviolet rays or heat, a quencher, dyes (dichroic dyes), a defoamer, a polymerizable compound, a polymerization initiator, a polymerization inhibitor, an antistatic agent, and a magnetic compound. (b) An element containing the above-described composition. (c) An element containing the above-described composition and used for controlling electromagnetic wave signals at any frequency from 1 GHz to 10 THz. (d) The above-described composition further containing a polymerizable compound, and an element containing this composition. (e) Use of the above-described composition as a composition having a nematic phase. (f) Use of an optically active composition obtained by adding an optically active compound to the above-described composition.

The liquid crystal composition of the disclosure has a large dielectric anisotropy and a small dielectric loss tangent (tan δ) in the frequency domain of electromagnetic wave signals in the range from 1 GHz to 10 THz. Thus, the liquid In Formula (1), $R^1$ is hydrogen, halogen, or alkyl having 1 to 12 carbon atoms, and in this alkyl, at least one $—CH_2—$ may be substituted with —O— or —S—, at least one $—(CH_2)_2—$ may be substituted with —CH═CH— or —C≡C—, and in these groups, at least one hydrogen may be substituted with halogen.

The preferable configuration of —CH═CH— in alkenyl depends on the position of the double bond. In alkenyl having a double bond at an odd-numbered position such as $—CH═CHCH_3$, $—CH═CHC_2H_5$, $—CH═CHC_3H_7$, $—CH═CHC_4H_9$, $—C_2H_4CH═CHCH_3$, or $—C_2H_4CH═CHC_2H_5$, a trans configuration is preferable. In alkenyl having a double bond at an even-numbered position such as $—CH_2CH═CHCH_3$, $—CH_2CH═CHC_2H_5$, or $—CH_2CH═CHC_3H_7$, a cis configuration is preferable. Alkenyl compounds having preferable configurations have a high clearing point or a wide temperature range of liquid crystal phase. Detailed descriptions are found in Mol. Cryst. Liq. Cryst., 1985, 131, 109 and Mol. Cryst. Liq. Cryst., 1985, 131, 327.

Preferable examples of $R^1$ are alkyl, alkoxy, alkoxyalkyl, alkenyl, alkynyl, and alkenyloxy. More preferable examples of $R^1$ are alkyl, alkoxy, alkenyl, and alkynyl.

Examples of alkyl are $—CH_3$, $—C_2H_5$, $—C_3H_7$, $—C_4H_9$, $—C_5H_{11}$, $—C_6H_{13}$, $—C_7H_{15}$, $—C_8H_{17}$, $—C_9H_{19}$, $—C_{10}H_{21}$, $—C_{11}H_{23}$, and $—C_{12}H_{25}$.

Examples of alkoxy are $—OCH_3$, $—OC_2H_5$, $—OC_3H_7$, $—OC_4H_9$, $—OC_5H_{11}$, $—OC_6H_{13}$, $—OC_7H_{15}$, $—OC_8H_{17}$, $—OC_9H_{19}$, $—OC_{10}H_{21}$, and $—OC_{11}H_{23}$.

Examples of alkoxyalkyl are $—CH_2OCH_3$, $—CH_2OC_2H_5$, $—CH_2OC_3H_7$, $—(CH_2)_2—OCH_3$, $—(CH_2)_2—OC_2H_5$, $—(CH_2)_2—OC_3H_7$, $—(CH_2)_3—OCH_3$, $—(CH_2)_4—OCH_3$, and $—(CH_2)_5—OCH_3$.

Examples of alkenyl are $—CH{=}CH_2$, $—CH{=}CHCH_3$, $—CH_2CH{=}CH_2$, $—CH{=}CHC_2H_5$, $—CH_2CH{=}CHCH_3$, $—(CH_2)_2—CH{=}CH_2$, $—CH{=}CHC_3H_7$, $—CH_2CH{=}CHC_2H_5$, $—(CH_2)_2—CH{=}CHCH_3$, and $—(CH_2)_3—CH{=}CH_2$.

Examples of alkynyl are $—C{\equiv}CH$, $—C{\equiv}CCH_3$, $—C{\equiv}CC_2H_5$, $—C{\equiv}CC_3H_7$, $—C{\equiv}CC_4H_9$, $—C{\equiv}CC_5H_{11}$, and $—C{\equiv}CC_6H_{13}$.

Examples of alkenyloxy are $—OCH_2CH{=}CH_2$, $—OCH_2CH{=}CHCH_3$, and $—OCH_2CH{=}CHC_2H_5$.

Examples of alkyl in which at least one hydrogen is substituted with halogen are $—CH_2F$, $—CHF_2$, $—CF_3$, $—(CH_2)_2—F$, $—CF_2CH_3$, $—CF_2CH_2F$, $—CF_2CHF_2$, $—CH_2CF_3$, $—CF_2CF_3$, $—(CH_2)_3—F$, $—CF_2CH_2CH_3$, $—CH_2CHFCH_3$, $—CH_2CF_2CH_3$, $—(CF_2)_3—F$, $—CF_2CHFCF_3$, $—CHFCF_2CF_3$, $—(CH_2)_4—F$, $—CF_2(CH_2)_2CH_3$, $—(CF_2)_4—F$, $—(CH_2)_5—F$, $—(CF_2)_5—F$, $—CH_2Cl$, $—CHCl_2$, $—CCl_3$, $—(CH_2)_2—Cl$, $—CCl_2CH_3$, $—CCl_2CH_2Cl$, $—CCl_2CHCl_2$, $—CH_2CCl_3$, $—CCl_2CCl_3$, $—(CH_2)_3—Cl$, $—CCl_2CH_2CH_3$, $—(CCl_2)_3—Cl$, $—CCl_2CHClCCl_3$, $—CHClCCl_2CCl_3$, $—(CH_2)_4—Cl$, $—(CCl_2)_4—Cl$, $—CCl_2(CH_2)_2CH_3$, $—(CH_2)_5—Cl$, and $—(CCl_2)_5—Cl$.

Examples of alkoxy in which at least one hydrogen is substituted with halogen are $—OCH_2F$, $—OCHF_2$, $—OCF_3$, $—O—(CH_2)_2—F$, $—OCF_2CH_2F$, $—OCF_2CHF_2$, $—OCH_2CF_3$, $—O—(CH_2)_3—F$, $—O—(CF_2)_3—F$, $—OCF_2CHFCF_3$, $—OCHFCF_2CF_3$, $—O(CH_2)_4—F$, $—O—(CF_2)_4—F$, $—O—(CH_2)_5—F$, $—O—(CF_2)_5—F$, $—OCH_2CHFCH_2CH_3$, $—OCH_2Cl$, $—OCHCl_2$, $—OCCl_3$, $—O—(CH_2)_2—Cl$, $—OCCk_2CH_2Cl$, $—OCCl_2CHCl_2$, $—OCH_2CCl_3$, $—O—(CH_2)_3—Cl$, $—O—(CCl_2)_3—Cl$, $—OCCl_2CHClCCl_3$, $—OCHClCCl_2CCl_3$, $—O(CH_2)_4—Cl$, $—O—(CCl_2)_4—Cl$, $—O—(CH_2)_5—Cl$, and $—O—(CCl_2)_5—Cl$.

Examples of alkenyl in which at least one hydrogen is substituted with halogen are $—CH{=}CHF$, $—CH{=}CF_2$, $—CF{=}CHF$, $—CH{=}CHCH_2F$, $—CH{=}CHCF_3$, $—(CH_2)_2—CH{=}CF_2$, $—CH_2CH{=}CHCF_3$, $—CH{=}CHCF_2CF_3$, $—CH{=}CHCl$, $—CH{=}CCl_2$, $—CCl{=}CHCl$, $—CH{=}CHCH_2Cl$, $—CH{=}CHCCl_3$, $—(CH_2)_2—CH{=}CCl_2$, $—CH_2CH{=}CHCCl_3$, and $—CH{=}CHCCl_2CCl_3$.

In Formula (1), $L^1$, $L^2$, $L^3$, and $L^4$ are hydrogen, fluorine, chlorine, methyl, or ethyl. Preferable examples of $L^1$ are fluorine or methyl, preferable examples of $L^2$ are hydrogen, fluorine, or methyl, preferable examples of $L^3$ are hydrogen, fluorine, methyl, or ethyl, and preferable examples of $L^4$ are hydrogen or methyl.

In Formula (1), $Y^1$ and $Y^2$ are hydrogen, fluorine, or ethyl. Preferable examples of $Y^1$ are hydrogen or fluorine, and preferable examples of $Y^2$ are hydrogen or fluorine.

In Formula (1), preferably, at least two among $L^1$, $L^2$, $L^3$, $L^4$, $Y^1$, and $Y^2$ are not hydrogen to lower the lower limit temperature. In addition, at least one among $L^1$, $L^2$, $L^3$, $L^4$, $Y^1$, and $Y^2$ is preferably fluorine.

In Formula (1), n is 0 or 1.

When n is 0, a case where any two of $L^1$, $L^2$, $L^3$, and $L^4$ are methyl and the remaining two are hydrogen, fluorine, chlorine, or ethyl does not exist. That is, when n is 0, a case where only any two of $L^1$, $L^2$, $L^3$, and $L^4$ are methyl does not exist. Specifically, a case where $L^1$ and $L^3$, $L^1$ and $L^4$, or $L^3$ and $L^4$ are simultaneously methyl does not exist. In addition, when n is 0 and $L^4$ is methyl, a case where $L^1$, $L^2$, $L^3$, $Y^1$, and $Y^2$ are simultaneously hydrogen does not exist.

As described above, a compound having desired physical properties can be obtained by appropriately selecting the types of terminal groups, bonding groups, etc. Since there is no significant difference in the physical properties of the compound, the compound (1) may contain isotopes such as $^2H$ (deuterium), $^{13}C$, etc. in amounts greater than their natural abundance ratios.

1-2. Preferable Embodiments of Compound (1)

Preferable embodiments of the compound (1) are a compound (1-1) to a compound (1-18).

(1-1)

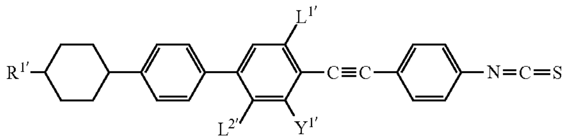

(1-2)

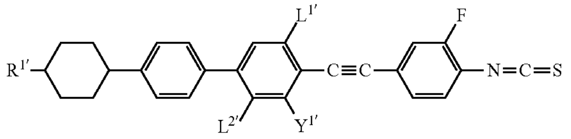

(1-3)

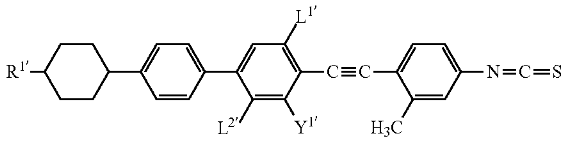

(1-4)

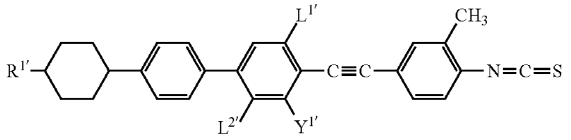

(1-5)

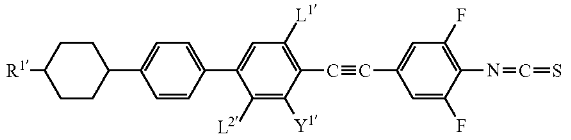

(1-6)

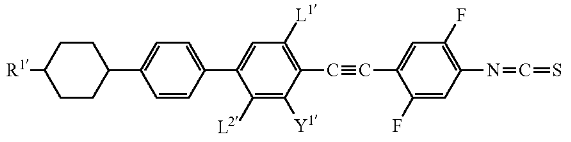

(1-7)

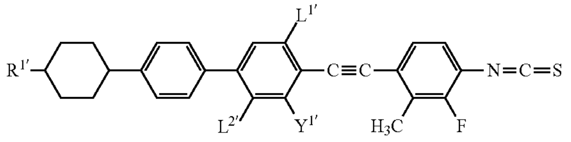

(1-8)

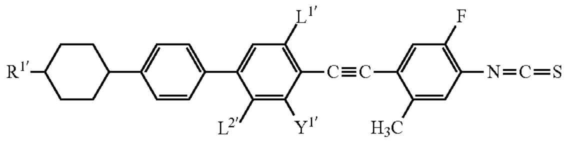

-continued (1-9)

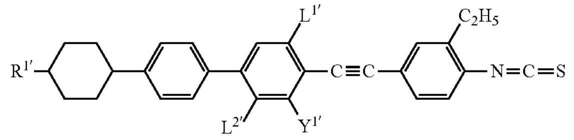

(1-10)

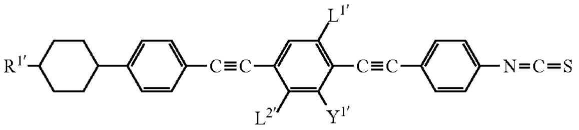

(1-11)

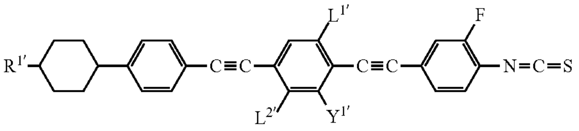

(1-12)

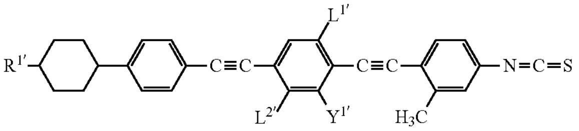

(1-13)

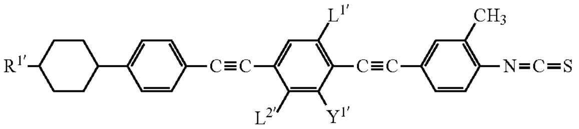

(1-14)

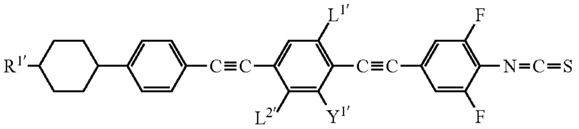

(1-15)

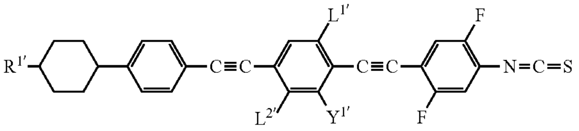

(1-16)

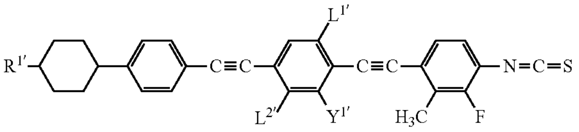

(1-17)

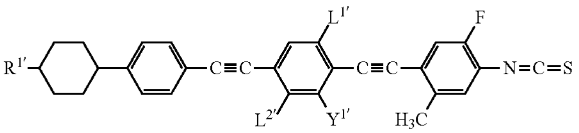

(1-18)

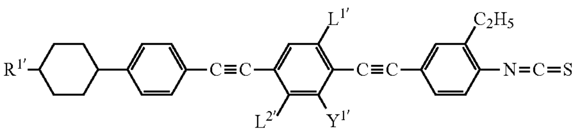

In Formula (1-1) to Formula (1-18), $R^{1'}$ is alkyl having 1 to 12 carbon atoms, and in this alkyl, at least one $—CH_2—$ may be substituted with —O— or —S—, at least one $—(CH_2)_2—$ may be substituted with —CH═CH— or —C≡C—, and in these groups, at least one hydrogen may be substituted with halogen;

$L^{1'}$ is fluorine or methyl, and $L^{2'}$ is hydrogen, fluorine, or methyl; and $Y^{1'}$ is hydrogen or fluorine.

1-3. Synthesis Method of Compound (1)

A synthesis method of the compound (1) will be described. The compound (1) may be synthesized by appropriately combining methods of organic synthetic chemistry. Methods for introducing desired terminal groups, rings, and bonding groups into starting materials are described in established texts such as Organic Syntheses (John Wiley & Sons, Inc), Organic Reactions (John Wiley & Sons, Inc), Comprehensive Organic Synthesis (Pergamon Press), and New Experimental Chemistry Course (Maruzen). Synthesis examples of the compound (1) are described in the section of Examples.

2. Composition

The composition of the disclosure will be described in the following order. First, configurations of component compounds in the composition will be described. Second, the main properties of the component compounds and the main effects of these compounds on the composition will be described. Third, combinations of components in the composition, preferable proportions of the components, and reasons thereof will be described. Fourth, preferable forms of the component compounds added will be described. Fifth, preferable embodiments of the component compounds added will be shown. Sixth, additives which may be added to the composition will be described. Finally, uses of the composition will be described.

First, configurations of component compounds in the composition will be described. The composition of the disclosure is classified into a composition A and a composition B. The composition A contains liquid crystalline compounds selected from a compound (1), a compound (2), and a compound (3), and may further contain other liquid crystalline compounds, additives, etc. "Other liquid crystalline compounds" are liquid crystalline compounds different from the compound (1), the compound (2), and the compound (3). Such compounds are mixed into the composition to further adjust properties. To prepare a liquid crystal composition having a desired refractive index anisotropy or a dielectric anisotropy at high frequencies, it is preferable not to use liquid crystalline compounds with a small refractive index anisotropy, such as one-ring compounds or two-ring compounds without bonding groups, as "other liquid crystalline compounds". The additives include an optically active compound, an antioxidant, an ultraviolet absorber, a stabilizer against ultraviolet rays or heat, a quencher, dyes (dichroic dyes), a defoaming agent, a polymerizable compound, a polymerization initiator, a polymerization inhibitor, an antistatic agent, a polar compound, etc.

The composition B consists substantially of the liquid crystalline compound selected from the compound (1), the compound (2), and the compound (3). "Substantially" means that the composition may contain additives, but does not contain other liquid crystalline compounds. The composition B has fewer components than the composition A. The composition B is preferable over the composition A from the viewpoint of cost reduction. The composition A is preferable over the composition B from the viewpoint that the properties thereof can be further adjusted by mixing other liquid crystalline compounds.

Second, the main properties of the component compounds and the main effects of these compounds on the properties of the composition will be described. The main properties of the component compounds are summarized in Table 1 based on the effects of the disclosure. Regarding the symbols in Table 1, L means large or high, M means medium, and S means small or low. The symbols L, M, and S are classifications based on qualitative comparisons among the component compounds, and 0 (zero) means that the value is approximately zero or close to zero.

TABLE 1

| Properties of compounds | | | |
|---|---|---|---|
| Compound | (1) | (2) | (3) |
| Upper limit temperature | L | S | M to L |
| Viscosity | L | S | M to L |
| Refractive index anisotropy | L | M | L |
| Dielectric anisotropy | M to L | M | M |

The main effects of the component compounds on the properties of the composition when the component compounds are mixed in the composition are as follows.

The compound (1) mainly has the effects of increasing the refractive index anisotropy of the liquid crystal composition, increasing the dielectric anisotropy, and increasing the upper limit temperature. By controlling the number of substituents on the benzene ring of the compound (1), the upper limit temperature and the lower limit temperature are controllable to some extent. In other words, upon decreasing the number of substituents, the upper limit temperature and the lower limit temperature tend to increase. Upon increasing the number of substituents, the upper limit temperature and the lower limit temperature tend to decrease.

The compound (2) mainly has the effects of increasing the refractive index anisotropy of the liquid crystal composition, increasing the dielectric anisotropy, and reducing the viscosity. The relationship between the number of substituents on the benzene ring and the upper limit temperature and the lower limit temperature is similar to that in the compound (1), and from the viewpoint of lowering the lower limit temperature of the liquid crystal composition, the number of substituents is preferably 1 or 2. From the viewpoint of reducing the viscosity, the number of substituents is preferably 1.

The compound (3) mainly has the effects of increasing the refractive index anisotropy of the liquid crystal composition, increasing the dielectric anisotropy, and increasing the upper limit temperature. The relationship between the number of substituents on the benzene ring and the upper limit temperature and the lower limit temperature is similar to that in the compound (1), and from the viewpoint of lowering the lower limit temperature of the liquid crystal composition, the number of substituents is preferably 2 or 3.

Third, combinations of components in the composition, preferable proportions of the component compounds, and reasons thereof will be described. The preferable combination of components in the composition is: compound (1)+compound (2)+compound (3), from the viewpoints of expanding the temperature range of the nematic phase, increasing the refractive index anisotropy and the dielectric anisotropy, and reducing the viscosity.

Based on the weight of the liquid crystal composition, a preferable proportion of the compound (1) is in a range from about 5 weight % to about 25 weight % to increase the refractive index anisotropy and increase $\Delta\varepsilon$ in the high frequency domain, while expanding the temperature range of the nematic phase. A more preferable proportion is in a range from about 5 weight % to about 20 weight %. A particularly preferable proportion is in a range from about 5 weight % to about 15 weight %.

Based on the weight of the liquid crystal composition, a preferable proportion of the compound (2) is in a range from about 10 weight % to about 55 weight % to increase the refractive index anisotropy and increase $\Delta\varepsilon$ in the high frequency domain, while expanding the temperature range of the nematic phase and reducing the viscosity. A more preferable proportion is in a range from about 20 weight % to about 50 weight %. A particularly preferable proportion is in a range from about 20 weight % to about 45 weight %.

Based on the weight of the liquid crystal composition, a preferable proportion of the compound (3) is in a range from about 20 weight % to about 50 weight % to increase the refractive index anisotropy and increase $\Delta\varepsilon$ in the high frequency domain, while expanding the temperature range of the nematic phase. A more preferable proportion is in a range from about 25 weight % to about 40 weight %. A particularly preferable proportion is in a range from about 25 weight % to about 35 weight %.

Fourth, preferable forms of the component compounds added will be described.

In a compound (2) and a compound (3), $R^2$ and $R^3$ are hydrogen, halogen, or linear alkyl having 1 to 12 carbon atoms, and in this alkyl, at least one $—CH_2—$ may be substituted with —O— or —S—, at least one $—(CH_2)_2—$ may be substituted with —CH═CH— or —C≡C—, and in these groups, at least one hydrogen may be substituted with halogen.

In the compound (2) and the compound (3), $R^2$ or $R^3$ is preferably methyl, ethyl, propyl, butyl, pentyl, hexyl, methoxy, or ethoxy to increase stability against ultraviolet rays or heat. To reduce the viscosity, methyl, ethyl, propyl, butyl, pentyl, methoxy, or ethoxy is preferable.

In a compound (2-1) to a compound (2-10) and a compound (3-1) to a compound (3-11), $R^{2'}$ and $R^{3'}$ are linear alkyl having 1 to 12 carbon atoms, and in this alkyl, at least one $—(CH_2)_2—$ may be substituted with —CH═CH— or —C≡C—.

In the compound (2) and the compound (3), $L^{21}$, $L^{22}$, $L^{23}$, $L^{31}$, $L^{32}$, and $L^{33}$ are hydrogen, halogen, alkyl having 1 to 3 carbon atoms, fluorinated alkyl having 1 to 3 carbon atoms, or cycloalkyl having 3 to 5 carbon atoms. Preferable $L^{21}$, $L^{22}$, $L^{23}$, $L^{31}$, $L^{32}$, and $L^{33}$ are hydrogen to increase the upper limit temperature, are fluorine or chlorine to increase the dielectric anisotropy, and are fluorine, chlorine, methyl, or ethyl to lower the lower limit temperature.

In the compound (2) and the compound (3), $Y^{21}$, $Y^{31}$, $Y^{32}$, $Y^{33}$, $Y^{34}$, $Y^{35}$, and $Y^{36}$ are hydrogen or halogen. Preferable $Y^{21}$, $Y^{31}$, $Y^{32}$, $Y^{33}$, $Y^{34}$, $Y^{35}$, and $Y^{36}$ are hydrogen to increase the refractive index anisotropy, and are fluorine or chlorine to increase the dielectric anisotropy and to lower the lower limit temperature.

In the compound (3-1) to the compound (3-11), $Y^{35'}$ is hydrogen, fluorine, or chlorine.

In the compound (2), at least one among $L^{21}$, $L^{22}$, and $L^{23}$ is preferably methyl to lower the lower limit temperature. In the compound (3), at least one among $L^{31}$, $L^{32}$, and $L^{33}$ is preferably methyl to lower the lower limit temperature.

In the compound (1), the compound (2), and the compound (3), to increase the dielectric anisotropy of the entire liquid crystal composition, $L^2$ and $Y^1$, $L^4$ and $Y^2$, $L^{21}$ and $L^{22}$, $L^{23}$ and $Y^{21}$, $Y^{33}$ and $Y^{35}$, $L^{31}$ and $L^{32}$, or $L^{33}$ and $Y^{36}$ are preferably not simultaneously halogen.

Fifth, preferable embodiments of the component compounds added will be shown.

Preferable compounds (2) are the compound (2-1) to the compound (2-10).

(2-1)

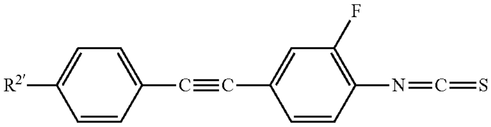

(2-2)

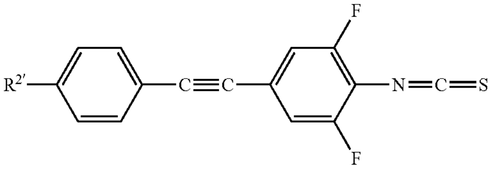

(2-3)

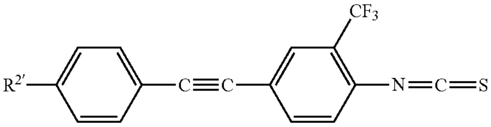

(2-4)

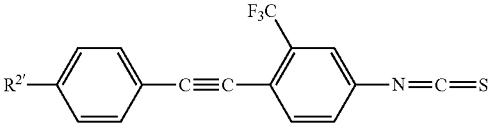

(2-5)

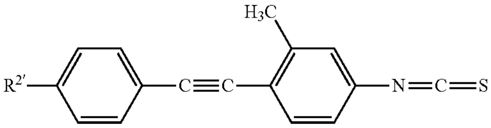

(2-6)

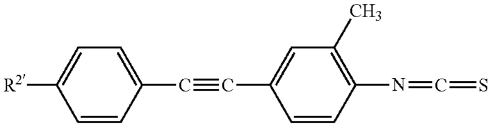

(2-7)

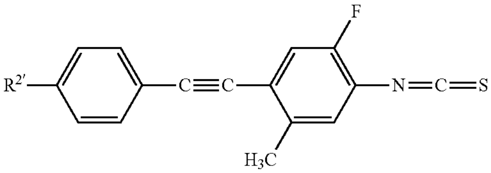

(2-8)

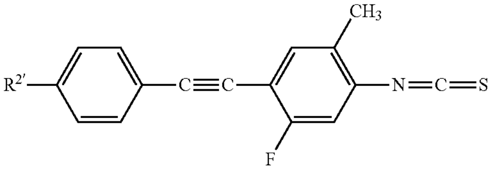

-continued (2-9)

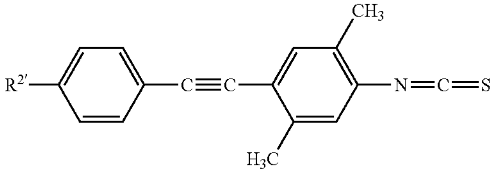

(2-10)

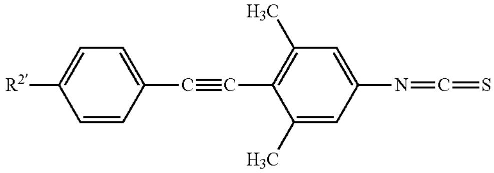

In Formula (2-1) to Formula (2-10), $R^{2'}$ is linear alkyl having 1 to 12 carbon atoms, and in this alkyl, at least one $-(CH_2)_2-$ may be substituted with $-CH{=}CH-$ or $-C{\equiv}C-$.

At least one of the compounds (2) is more preferably the compound (2-2), the compound (2-5), or the compound (2-6).

Preferable compounds (3) are the compound (3-1) to the compound (3-11).

(3-1)

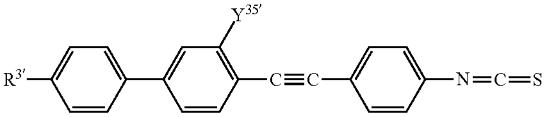

(3-2)

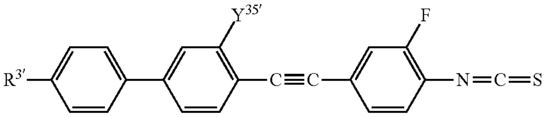

(3-3)

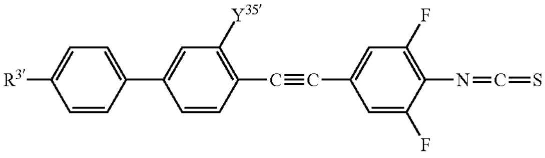

(3-4)

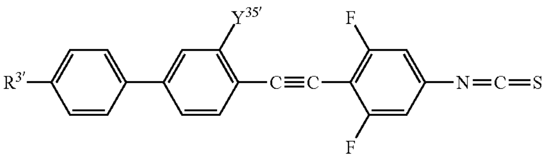

(3-5)

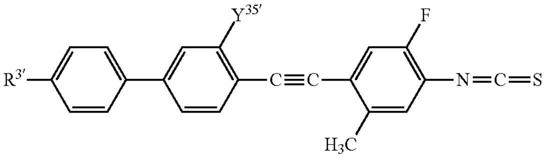

-continued (3-6)

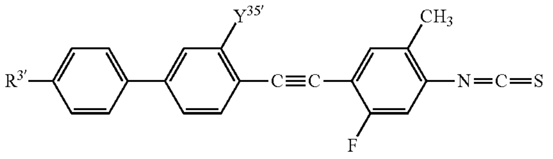

(3-7)

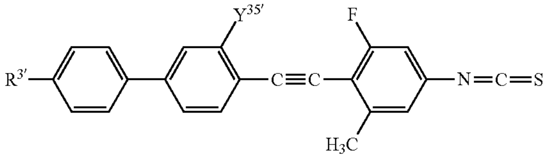

(3-8)

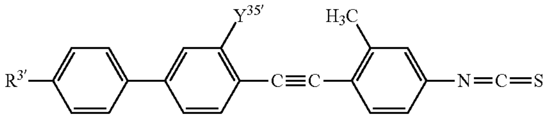

(3-9)

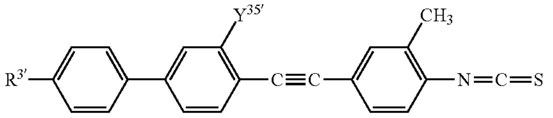

(3-10)

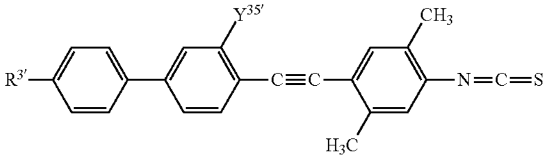

(3-11)

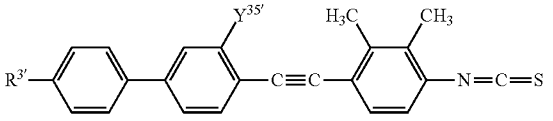

In Formula (3-1) to Formula (3-11), $R^{3'}$ is linear alkyl having 1 to 12 carbon atoms, and in this alkyl, at least one $—(CH_2)_2—$ may be substituted with $—CH{=}CH—$ or $—C{\equiv}C—$; $Y^{35'}$ is hydrogen, fluorine, or chlorine.

At least one of the compounds (3) is more preferably the compound (3-3), the compound (3-5), the compound (3-8), the compound (3-9), or the compound (3-10).

Sixth, additives which may be added to the composition will be described. Such additives include an optically active compound, an antioxidant, an ultraviolet absorber, a stabilizer against ultraviolet rays or heat, a quencher, dyes (dichroic dyes), a defoamer, a polymerizable compound, a polymerization initiator, a polymerization inhibitor, an antistatic agent, a polar compound, etc. Hereinafter, the mixing proportion of these additives will be a proportion (weight) based on the weight of the liquid crystal composition unless otherwise specified.

Any combination of additives may be used, and for example, it is also possible to use a combination of different types of antioxidants. For example, it is also possible to use a combination of different types of additives, for example, using an antioxidant, an ultraviolet absorber, and further a stabilizer in combination.

An optically active compound is added to the composition to induce a helical structure of liquid crystals to give a twist angle. Examples of such a compound include a compound (8-1) to a compound (8-5). A preferable proportion of the optically active compound is about 5 weight % or less. A more preferable proportion thereof is in a range from about 0.01 weight % to about 2 weight %.

(8-1)

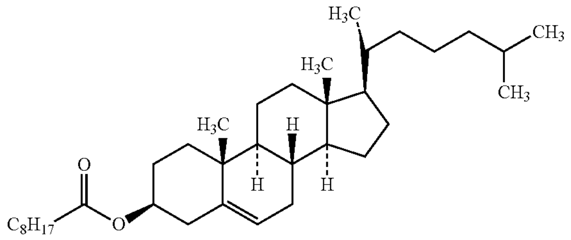

(8-2)

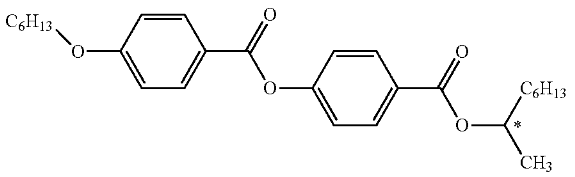

(8-3)

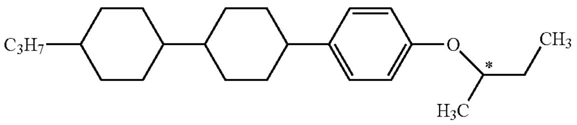

(8-4)

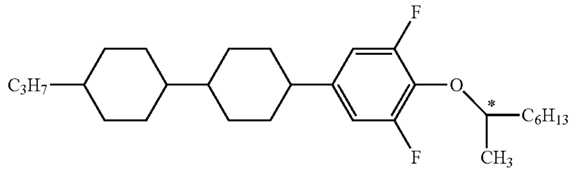

(8-5)

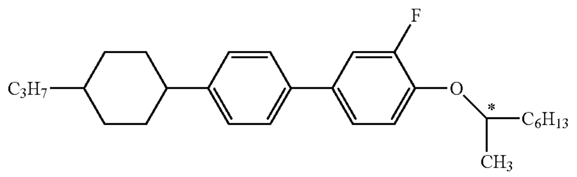

To prevent a decrease in specific resistance due to heating in atmospheric air or to maintain a large voltage holding ratio not only at room temperature but also at temperatures close to the upper limit temperature after long-term use of an element, an antioxidant is added to the composition. Preferable examples of the antioxidant include a compound (9) in which t is an integer of 1 to 9.

(9)

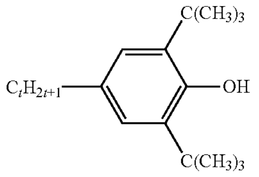

In the compound (9), t is preferably 1, 3, 5, 7, or 9. t is more preferably 7. Since the compound (9) in which t is 7 has low volatility, it is effective to maintain a large voltage holding ratio not only at room temperature but also at temperatures close to the upper limit temperature after long-term use of an element. A preferable proportion of the antioxidant is about 50 ppm or higher to obtain effect thereof, and is about 600 ppm or lower so as not to lower the upper limit temperature or increase the lower limit temperature. A more preferable proportion thereof is in a range from about 100 ppm to about 300 ppm.

Preferable examples of the ultraviolet absorber include benzophenone derivatives, benzoate derivatives, triazole derivatives, etc. Light stabilizers such as sterically hindered amines are also preferable. Preferable examples of the light stabilizer include a compound (10-1) to a compound (10-16). A preferable proportion of such an absorber or stabilizer is about 50 ppm or higher to obtain effect thereof, and is about 10,000 ppm or lower so as not to lower the upper limit temperature or increase the lower limit temperature. A more preferable proportion thereof is in a range from about 100 ppm to about 10,000 ppm.

(10-1)

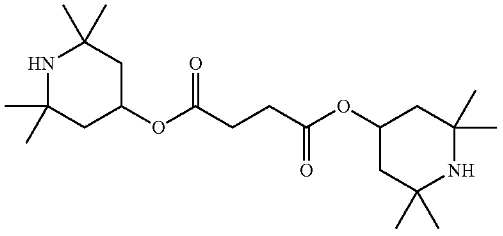

(10-2)

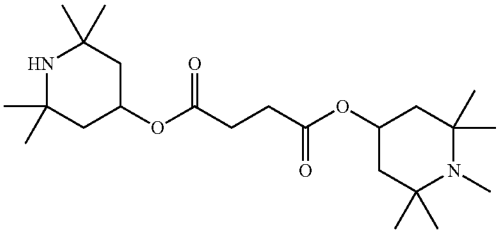

(10-3)

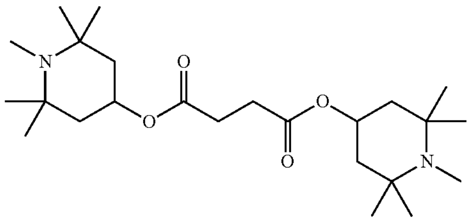

(10-4)

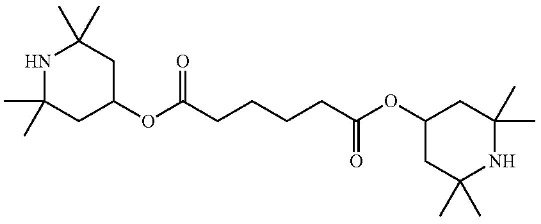

(10-5)

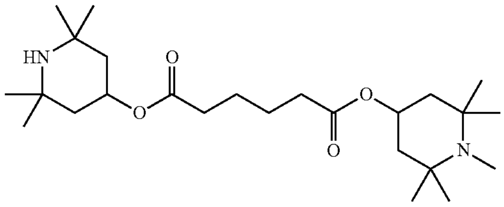

(10-6)

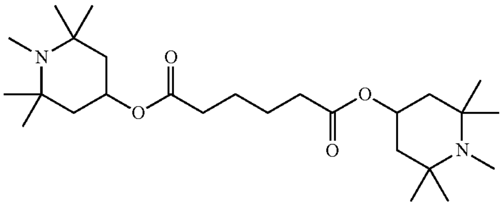

(10-7)

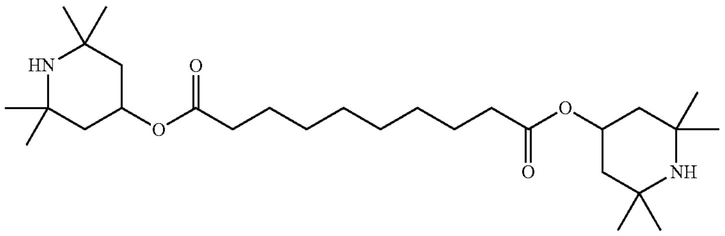

(10-8)

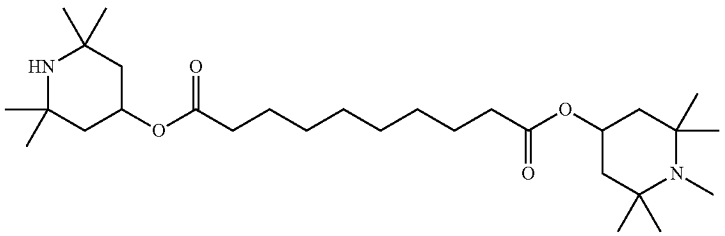

-continued
(10-9)
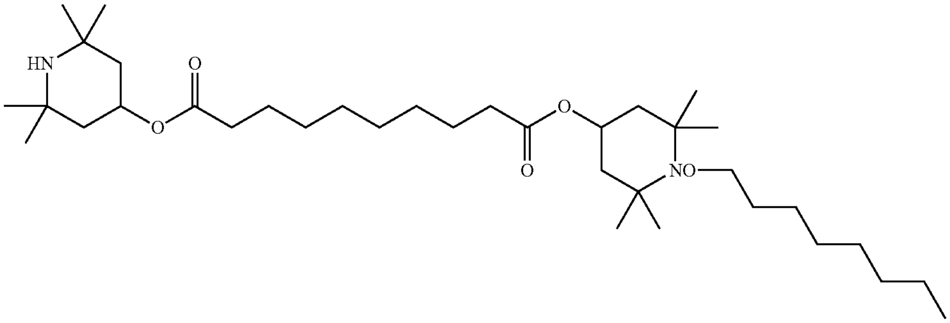
(10-10)
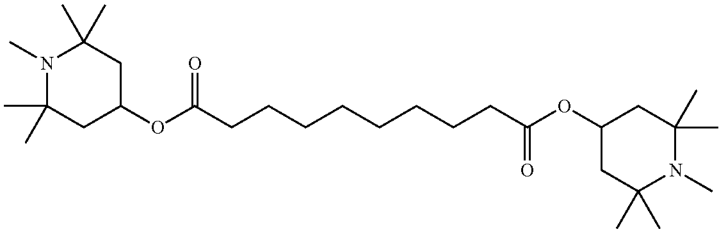
(10-11)
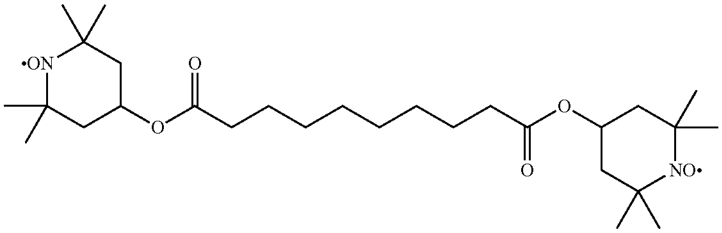
(10-12)
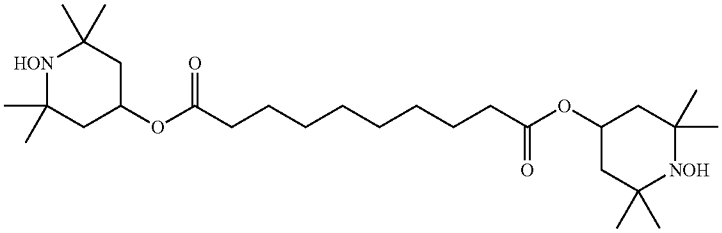
(10-13)
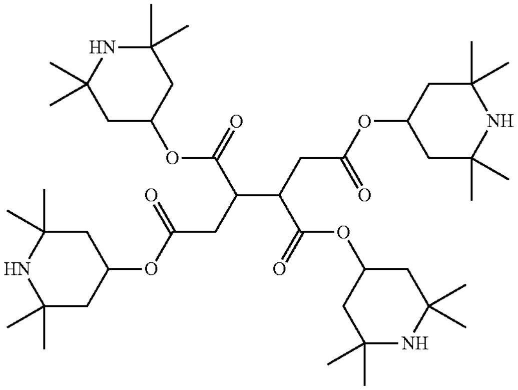
(10-14)
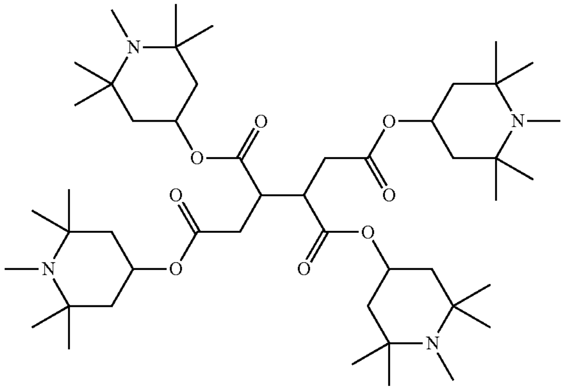

-continued (10-15)

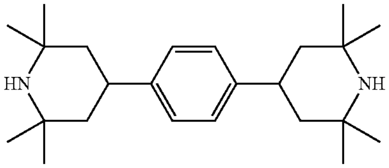

(10-16)

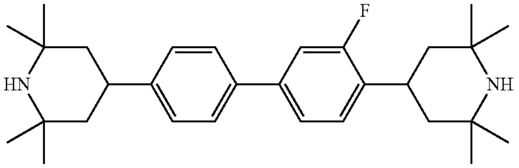

Additives preferable as the stabilizer against ultraviolet rays or heat include amino-tolane compounds represented by a compound (11) (specification of U.S. Pat. No. 6,495,066).

(11)

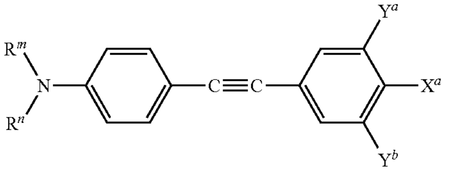

In Formula (11), $R^m$ and $R^n$ are alkyl having 1 to 12 carbon atoms, alkoxy having 1 to 12 carbon atoms, alkenyl having 2 to 12 carbon atoms, or alkenyloxy having 2 to 12 carbon atoms; $X^a$ is —$NO_2$, —C≡N, —N═C═S, fluorine, or —$OCF_3$; and $Y^a$ and $Y^b$ are hydrogen or fluorine. A preferable proportion of such stabilizers is in a range from 1 weight % to 20 weight % and more preferably in a range from 5 weight % to 10 weight % to obtain effects thereof.

A quencher is a compound that receives light energy absorbed by a liquid crystalline compound and converts it to heat energy to prevent decomposition of a liquid crystalline compound. A preferable proportion of such a quencher is about 50 ppm or higher to obtain effect thereof, and is about 20,000 ppm or lower to lower the lower limit temperature. A more preferable proportion thereof is in a range from about 100 ppm to about 10,000 ppm.

Dichroic dyes such as azo-based dyes and anthraquinone-based dyes are added to the composition to make it suitable for guest host (GH) mode elements. A preferable proportion of the dyes is in a range from about 0.01 weight % to about 10 weight %. A defoamer such as dimethyl silicone oil and methylphenyl silicone oil are added to the composition to prevent foaming. A preferable proportion of the defoamer is about 1 ppm or higher to obtain effect thereof, and is about 1,000 ppm or lower to prevent display defects. A more preferable proportion thereof is in a range from about 1 ppm to about 500 ppm.

A polymerizable compound is added to the composition to make it suitable for polymer-stabilized elements. Preferable examples of the polymerizable compound include compounds having polymerizable groups such as acrylates, methacrylates, vinyl compounds, vinyloxy compounds, propenyl ethers, epoxy compounds (oxiranes and oxetanes), and vinyl ketone. More preferable examples include derivatives of acrylates or methacrylates. A preferable proportion of the polymerizable compound is about 0.05 weight % or more to obtain effect thereof, and is about 20 weight % or less to prevent an increase in driving temperature. A more preferable proportion thereof is in a range from about 0.1 weight % to about 10 weight %. The polymerizable compound is polymerized through ultraviolet irradiation. Polymerization may be carried out in the presence of a polymerization initiator such as a photopolymerization initiator. Suitable conditions for polymerization, suitable types of initiators, and suitable amounts thereof are known to those skilled in the art and described in documents. For example, photopolymerization initiator Irgacure 651 (registered trademark; BASF), Irgacure 184 (registered trademark; BASF), or Darocur 1173 (registered trademark; BASF) is suitable for radical polymerization. A preferable proportion of the photopolymerization initiator is in a range from about 0.1 parts by weight to about 5 parts by weight based on 100 parts by weight of the polymerizable compound. A more preferable proportion thereof is in a range from about 1 part by weight to about 3 parts by weight.

A polymerization inhibitor may be added to prevent polymerization during storage of a polymerizable compound. A polymerizable compound is generally added to the composition without removing a polymerization inhibitor. Examples of the polymerization inhibitor include hydroquinone, hydroquinone derivatives such as methylhydroquinone, 4-tert-butylcatechol, 4-methoxyphenol, and phenothiazine.

A polar compound in this specification is an organic compound having polarity and does not include a compound having an ionic bond. Atoms such as oxygen, sulfur, and nitrogen are more electronegative and tend to have a partial negative charge. Carbon and hydrogen tend to be neutral or have a partial positive charge. Polarity results from uneven distribution of partial charges between different atoms in a compound. For example, the polar compound has at least one substructure such as —OH, —COOH, —SH, —$NH_2$, >NH, and >N—.

Finally, uses of the composition will be described. Since the composition of the disclosure has a lower limit temperature of about −10° C. or lower and an upper limit temperature of about 70° C. or higher, the composition of the disclosure may be used not only as a composition having a nematic phase, but also used as an optically active composition upon adding an optically active compound.

An oriented liquid crystal composition has different dielectric constants in a vertical direction and a horizontal direction. For this reason, it has a property of dielectric anisotropy.

Not only antenna elements but elements using a liquid crystal composition are also generally elements which are formed by sandwiching a liquid crystal composition as a layer between two substrates, and in which liquid crystal molecules are aligned (oriented) in one direction due to orientation films at interfaces. In the case where there is no external field, liquid crystal molecules in an element are aligned in one direction due to orientation control force of the orientation films. However, when an external field is applied, the liquid crystal molecules in the element deviate from the alignment of the orientation films and face the direction of the external field. In addition, when the external field is removed again, the liquid crystal molecules return to their original states of being aligned in one direction due to the orientation control force of the orientation films. In this manner, the orientation of the liquid crystal molecules in the element can be controlled by the orientation and magnitude of the external field, thereby controlling the inclination (angle) of the liquid crystal molecules in the element with respect to the one direction. Since the liquid crystal composition has dielectric anisotropy, it is possible to control the dielectric constant of the layer of liquid crystal composition in the element with respect to the one direction by controlling the angle of the liquid crystal molecules in the element with respect to the one direction. For example, if the dielectric constant of a layer of liquid crystal composition in an element in one direction when there is no external field is a dielectric constant in the vertical direction of the liquid crystal composition, an external field can be applied thereto perpendicularly to the one direction to change the dielectric constant to a dielectric constant in the horizontal direction of the liquid crystal composition.

In this manner, the liquid crystal composition of the disclosure may be used in a switching element capable of reversibly controlling a dielectric constant by reversibly changing the orientation direction of liquid crystal molecules.

Angles of liquid crystal molecules in an element can be controlled using an electric field as an external field. A voltage required to drive liquid crystal molecules is a driving voltage. To control angles of liquid crystal molecules, it is required for dielectric anisotropy of a liquid crystal composition at 25° C. to be larger than at least 2 in a frequency range below 1 MHz. To further reduce the driving voltage, it is necessary to increase the dielectric anisotropy at 25° C. in the frequency range below 1 MHz, preferably to 5 or more, and more preferably to 10 or more.

As described above, the larger the refractive index anisotropy (Δn) in visible light (e.g., a wavelength of 589 nm), the larger the dielectric anisotropy (Δε) in the high-frequency domain (a range from microwaves to terahertz waves (approximately 10 THz)). The liquid crystal composition containing the compounds represented by Formula (1) of the disclosure preferably has a refractive index anisotropy (Δn) of 0.30 or more at 25° C. In particular, when used for high-frequency applications, Δn is more preferably 0.40 or more, and particularly preferably 0.45 or more.

To perform phase difference control in the high-frequency domain, the dielectric anisotropy in the high-frequency domain is preferably 0.5 or more. To perform phase control more suitably, it is necessary to increase the dielectric anisotropy in the high-frequency domain. To perform sufficient phase control, the dielectric anisotropy is preferably 1.0 or more, and more preferably 1.2 or more.

Furthermore, the composition of the disclosure may be used in elements for controlling electromagnetic waves in the frequency range from 1 GHz to 10 THz. Application examples thereof include not only antenna arrays and electromagnetic wave reflectors, but also millimeter-wave variable phase shifters, millimeter-wave radars, etc. Elements utilizing the composition of the disclosure are being developed for various applications and methods. For antenna arrays, antenna arrays applying metamaterial technology are being developed. For electromagnetic wave reflectors, intelligent reflecting surfaces (IRS), reconfigurable intelligent surface (RIS) reflectors, and frequency selective surfaces are being developed.

Elements containing this composition may also be used for applications other than electromagnetic wave control. By reversibly changing the orientation direction of the liquid crystal molecules, not only the dielectric constant but also the refractive index can be controlled. The liquid crystal composition according to the disclosure exhibits a high refractive index anisotropy (Δn), and thus, the amount of change in refractive index and the amount of phase modulation caused by changing the orientation direction of liquid crystal molecules in visible light and infrared light are large, and can be controlled.

Application examples of these property controls include birefringent lenses for stereoscopic image display used as switchable 2D/3D lenses, liquid crystal lenses used for camera focus adjustment, etc. In addition, it is also possible to use them in spatial light modulators (SLMs) used in electronic holographic displays, and in LiDAR (Light Detection And Ranging) elements, which are distance measuring sensors.

EXAMPLES

The disclosure will be described in more detail with reference to Examples. The disclosure is not limited by these Examples. The disclosure also includes mixtures obtained by mixing at least two compositions of Examples. The synthesized compounds were identified by NMR analysis. The properties of the compositions were measured according to methods described below.

NMR analysis: The measurement instrument used was DRX-500 (manufactured by Bruker BioSpin Corporation). For $^{1}$H-NMR measurements, the sample was dissolved in a deuterated solvent such as $CDCl_3$, and the measurement was performed at room temperature, at 500 MHz, with a cumulative count of 16 scans. Tetramethylsilane was used as an internal standard. For $^{19}$F-NMR measurements, $CFCl_3$ was used as an internal standard, and the measurement was performed with a cumulative count of 24 scans. In the description of nuclear magnetic resonance spectra, s means singlet, d means doublet, t means triplet, q means quartet, quin means quintet, sex means sextet, m means multiplet, and br means broad.

Measurement samples: When measuring α phase structure and a transition temperature, the liquid crystalline compound itself was used as the sample. When measuring physical properties such as an upper limit temperature of a nematic phase, a viscosity, an optical anisotropy, a dielectric anisotropy, etc., a composition prepared by mixing the compound with a base liquid crystal was used as the sample.

In the case of using a sample prepared by mixing the compound with a base liquid crystal, the measurement was performed according to the following method. A sample was prepared by mixing 20 weight % of the compound and 80 weight % of the base liquid crystal. Based on the measured value of this sample, an extrapolated value was calculated according to the extrapolation method expressed by the following equation, and the extrapolated value was recorded. <Extrapolated value>=(100×<Measured value of sample>−<Weight % of base liquid crystal>×<Measured value of base liquid crystal>)/<Weight % of compound>

In the case where crystals (or smectic phase) precipitated at 25° C. even with this proportion of the compound to the base liquid crystal, the proportion of the compound to the base liquid crystal was changed in the order of 10 weight %:90 weight %, 5 weight %:95 weight %, and 1 weight %:99 weight %, and the physical properties of the sample were measured at the proportion at which crystals (or smectic phase) no longer precipitated at 25° C. Unless otherwise specified, the proportion of the compound to the base liquid crystal is 20 weight %:80 weight %.

A base liquid crystal (i) below was used as the base liquid crystal. Proportions of components of the base liquid crystal (i) are shown in weight %.

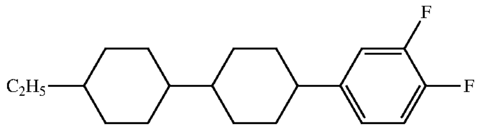

16.67wt %

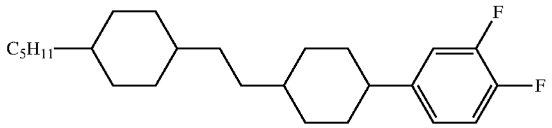

10.00wt %

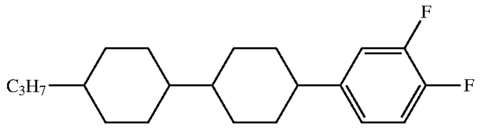

16.67wt %

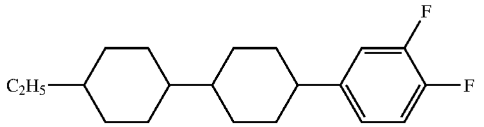

6.25wt %

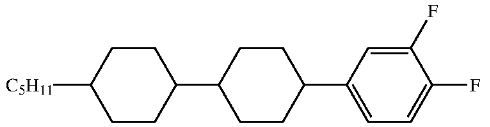

16.66wt %

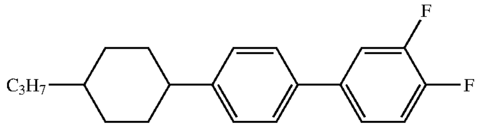

6.25wt %

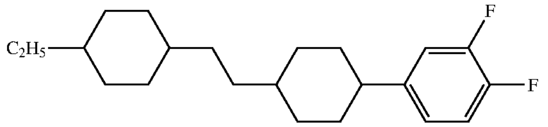

10.00wt %

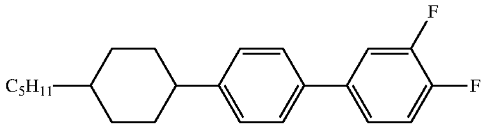

12.50wt %

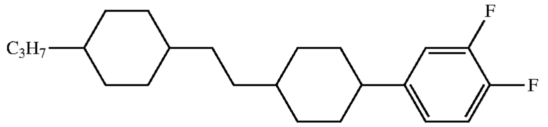

5.00wt %

Measurement methods: The properties were measured according to the following methods. Most of these were methods described in Japan Electronics and Information Technology Industries Association (hereinafter referred to as JEITA) standards (JEITA·ED-2521B) deliberated and established by the JEITA, or modified methods thereof. A thin film transistor (TFT) was not attached to a TN cell used for the measurement.

Upper Limit Temperature (NI; ° C.) of Nematic Phase:

A sample was placed on a hot plate of a melting-point measurement apparatus including a polarizing microscope, and heated at a rate of 1° C./min. The temperature was measured when a part of the sample changed from the nematic phase to an isotropic liquid.

Lower Limit Temperature (Tc; ° C.) of Nematic Phase:

Samples having a nematic phase were placed in glass bottles and stored in freezers at 0° C., −10° C., −20° C., −30° C. and −40° C. for 10 days, and then the liquid crystal phases were observed. For example, when the sample remained in the nematic phase at −20° C. and changed to a crystalline or smectic phase at −30° C., Tc was recorded as $<-20$° C.

Viscosity (bulk viscosity; f; measured at 20° C.; mPa·s):

An E-type rotational viscometer manufactured by Tokyo Keiki Inc. was used for measurement.

Viscosity (Rotational Viscosity; 71; Measured at 25° C.; mPa·s):

The measurement was performed according to the method described in M. Imai et al., Molecular Crystals and Liquid Crystals, Vol. 259, 37 (1995). The sample was placed in a TN cell with a twist angle of 0° and a gap (cell gap) of 5 m between two glass substrates. Voltage was applied to this cell in steps of 0.5 V in a range from 16 V to 19.5 V. After 0.2 seconds of non-application, an application was repeated under conditions of a single rectangular wave (rectangular pulse; 0.2 seconds) and non-application (2 seconds). A peak current and a peak time of a transient current generated by this application were measured. A value of a rotational viscosity was obtained based on these measured values and Calculation Formula (8) described on page 40 of the paper of M. Imai et al. A value of a dielectric anisotropy required for this calculation was obtained according to a method described below using the cell used for measuring this rotational viscosity.

Refractive Index Anisotropy (in the Case of $\Delta n<0.30$; Measured at 25° C.):

The measurement was performed with an Abbe refractometer having a polarizing plate attached to an eyepiece, using light at a wavelength of 589 nm. After rubbing the surface of a main prism in one direction, a sample was added dropwise onto the main prism. A refractive index $n_{//}$ was measured when the direction of polarization was parallel to the rubbing direction. A refractive index $n_{\perp}$ was measured when the direction of polarization was perpendicular to the rubbing direction. A value of a refractive index anisotropy was calculated according to an equation: $\Delta n=n_{//}-n_{\perp}$.

Refractive Index Anisotropy (in the Case of $\Delta n\geq 0.30$; Measured at 25° C.):

A sample was placed in an element composed of two glass substrates and oriented antiparallel. A thickness direction retardation (Rth) of this element was measured using a phase difference film/optical material inspection device (manufactured by Otsuka Electronics Co., Ltd., product name: RETS-100), and a refractive index anisotropy (Δn) was calculated based on the retardation value (Rth) and a gap (d: cell gap) between the glass substrates according to the following equation. The wavelength of light used was 589 nm.

$$Rth=\Delta n\cdot d$$

Dielectric Anisotropy (Δε; Measured at 25° C.):

A sample was placed in a TN cell in which the gap (cell gap) between two glass substrates was 9 μm and the twist angle was 80 degrees. A sine wave (10 V, 1 kHz) was applied to this cell, and after 2 seconds, a dielectric constant ($\varepsilon_{//}$) in a major axis direction of liquid crystal molecules was measured. A sine wave (0.5 V, 1 kHz) was applied to this cell, and after 2 seconds, a dielectric constant ($\varepsilon_{\perp}$) in a minor axis direction of liquid crystal molecules was measured. The value of the dielectric anisotropy was calculated according to an equation: $\Delta\varepsilon=\varepsilon_{//}-\varepsilon_{\perp}$.

Voltage Holding Ratio (VHR; Measured at 25° C.; %):

A cell used for measurement had the following structure. Specifically, an ITO electrode and a rubbed polyimide orientation film were disposed sequentially on each substrate. Two such substrates were bonded together with the orientation film surfaces facing inward such that an angle of rubbing directions between the upper and lower substrates was 90 degrees. The gap (cell gap) between the two glass substrates was 5 m. The liquid crystal composition was sealed in this cell. This TN cell was charged by applying a pulse voltage (5 V for 60 microseconds). A decaying voltage was measured for 16.7 milliseconds with a high-speed voltmeter, and an area A between a voltage curve and a horizontal axis in a unit period was obtained. Δn area B was an area in the case where there was no decay. A voltage holding ratio was expressed as a percentage of the area A to the area B.

Dielectric Anisotropy at 28 GHz (Measured at Room Temperature):

For a dielectric anisotropy at 28 GHz (Δε@28 GHz), a variable short-circuit waveguide to which a window material was attached was filled with liquid crystals according to a method disclosed in Applied Optics, Vol. 44, No. 7, p. 1150 (2005) and held in a static magnetic field of 0.3 T for 3 minutes. A microwave of 28 GHz was inputted to the waveguide, and an amplitude ratio of a reflected wave to an incident wave was measured. The measurement was performed by changing an orientation of the static magnetic field and a tube length of the short-circuit unit to determine refractive indices (n: ne, no) and loss parameters (α: αe, αo).

For calculation of a complex dielectric constant (ε', ε"), the calculated refractive indices, the loss parameters, and the following relational expressions were used.

$$\varepsilon' = n^2 - \kappa^2$$

$$\varepsilon'' = 2n\kappa$$

$$\alpha = 2\omega\kappa/c$$

Herein, c is a light velocity in vacuum, ω is an angular velocity, and κ is an extinction coefficient. $\varepsilon'_{//}$ was calculated based on ne, $\varepsilon'_{\perp}$ was calculated based on no, and the dielectric anisotropy (Δε@28 GHz) was calculated according to: $\varepsilon'_{//}-\varepsilon'_{\perp}$.

Dielectric Loss Tangent at 28 GHz (Tan δ; Measured at Room Temperature):

A dielectric loss tangent at 28 GHz (tan δ@28 GHz) was calculated based on ε"/ε' using the complex dielectric constant (ε', ε"). Since anisotropy also appeared in tan δ, a larger value was recorded.

Example 1

Synthesis of a Compound (1-6): 4-((2,5-difluoro-4-isothiocyanatophenyl)ethynyl)-3-fluoro-4'-(4-pentylcyclohexyl)-1,1'-biphenyl

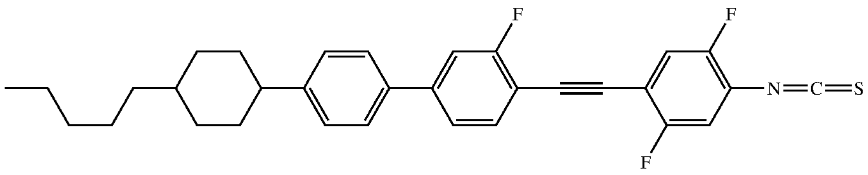

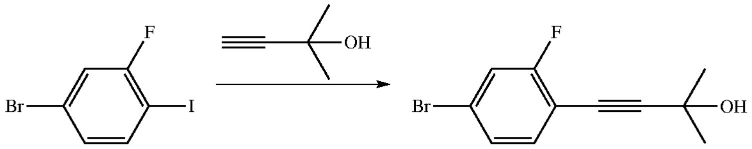

(intermediate 1)

Commercially available raw materials 1-bromo-3-fluoro-4-iodobenzene (50 g), triethylamine (150 mL), and THF (100 mL) were transferred to a reaction vessel, and a THF (50 mL) solution of 2-methyl-3-butyn-2-ol (15.1 g) was transferred to a dripping funnel and attached to the reaction vessel to perform nitrogen substitution. Catalysts CuI (0.6 g) and $PdCl_2(PPh_3)_2$ (1.2 g) were added, and dropwise addition was started while stirring at room temperature. After completion of the dropwise addition, stirring was performed at room temperature for 2 hours. Pure water, ammonium chloride, and toluene were added to the reaction solution, the organic layer was washed twice with pure water, and the organic layer was concentrated. The product was purified by silica gel column chromatography (developing liquid: toluene) and recrystallized from heptane to obtain an intermediate 1 (40.7 g).

The structure of the obtained compound was confirmed by NMR measurement.

$^1$H-NMR (δ ppm: $CDCl_3$): 7.28-7.21 (m, 3H), 2.24 (s, 1H), 1.63 (s, 6H).

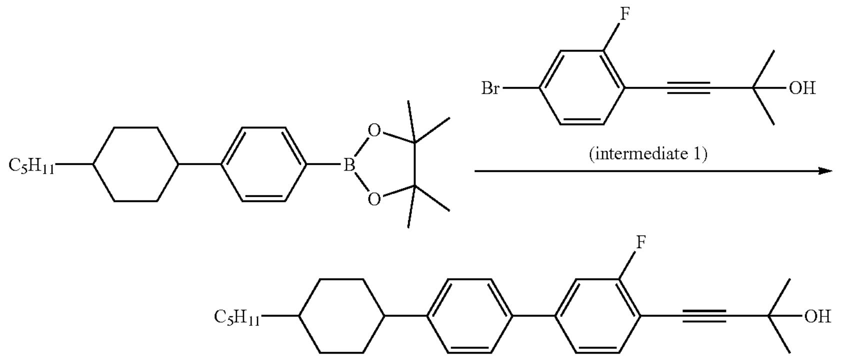

(intermediate 2)

Under nitrogen atmosphere, Pd-132 (Johnson Matthey) (1.0 g) was added to 4,4,5,5-tetramethyl-2-(4-(4-pentylcyclohexyl)phenyl)-1,3,2-dioxaborolane (50 g), the intermediate 1 (36.1 g), potassium carbonate (38.8 g), toluene (350 mL), ethanol (150 mL), and pure water (150 mL), and heated and stirred at 80° C. for 1 hour. After cooling to room temperature, pure water and toluene were added, the organic layer was washed with pure water and concentrated. The obtained solid was purified by silica gel column chromatography (developing liquid: toluene) and recrystallized from boiling toluene/heptane=4/6 (volume ratio) to obtain an intermediate 2 (44 g).

The structure of the obtained compound was confirmed by NMR measurement.

$^1$H-NMR (δ ppm: $CDCl_3$): 7.49 (d, 2H), 7.44 (t, 1H), 7.33-7.27 (m, 4H), 2.51 (tt, 1H), 2.08 (s, 1H), 1.90 (m, 4H), 1.65 (s, 6H), 1.47 (m, 2H), 1.37-1.20 (m, 9H), 1.06 (m, 2H), 0.90 (t, 3H).

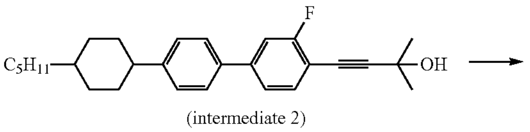

(intermediate 2)

-continued

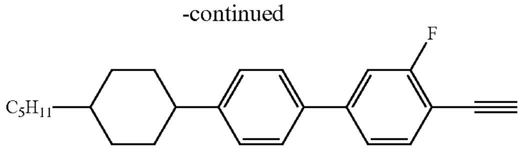

(intermediate 3)

Under nitrogen atmosphere, KOH (6.7 g) was added to the intermediate 2 (44 g) and toluene (440 mL) and heated and stirred at 120° C. for 2 hours. After cooling to room temperature, the mixture was neutralized with dilute hydrochloric acid, and the organic layer was washed twice with pure water and concentrated. The obtained solid was purified by silica gel column chromatography (developing liquid: toluene/heptane=1/9 (volume ratio)) and recrystallized from heptane to obtain an intermediate 3 (29 g).

The structure of the obtained compound was confirmed by NMR measurement.

$^1$H-NMR (δ ppm: $CDCl_3$): 7.51 (t, 1H), 7.49 (d, 2H), 7.34-7.28 (m, 4H), 3.34 (s, 1H), 2.51 (tt, 1H), 1.91 (m, 4H), 1.48 (m, 2H), 1.37-1.20 (m, 9H), 1.06 (m, 2H), 0.90 (t, 3H).

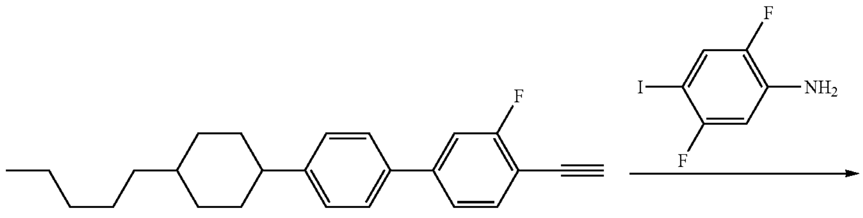

(intermediate 3)

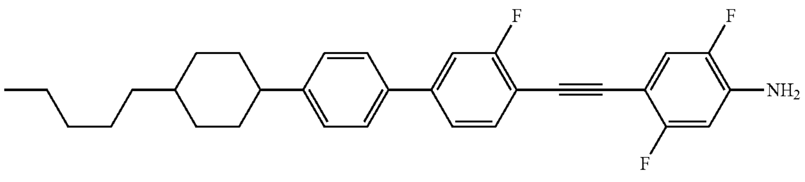

(intermediate 4)

Under nitrogen atmosphere, CuI (0.07 g) and $Pd(PPh_3)_4$ (0.22 g) were added to 2,5-difluoro-4-iodoaniline (4.5 g), the intermediate 3 (7 g), triethylamine (20 mL), and THF (20 mL) and heated and stirred at 40° C. for 1 hour. Pure water, ammonium chloride, and toluene were added to the reaction solution, the organic layer was washed twice with pure water, and the organic layer was concentrated. The product was purified by silica gel column chromatography (developing liquid:toluene) and recrystallized from toluene/heptane=15/85 (volume ratio) to obtain an intermediate 4 (8.9 g).

The structure of the obtained compound was confirmed by NMR measurement.

$^1$H-NMR (δ ppm: $CDCl_3$): 7.53 (t, 1H), 7.51 (d, 2H), 7.35 (dd, 1H), 7.32 (dd, 1H), 7.29 (d, 2H), 7.14 (dd, 1H), 6.50 (dd, 1H), 4.03 (s, 2H), 2.51 (tt, 1H), 1.90 (m, 4H), 1.47 (m, 2H), 1.37-1.20 (m, 9H), 1.06 (m, 2H), 0.90 (t, 3H).

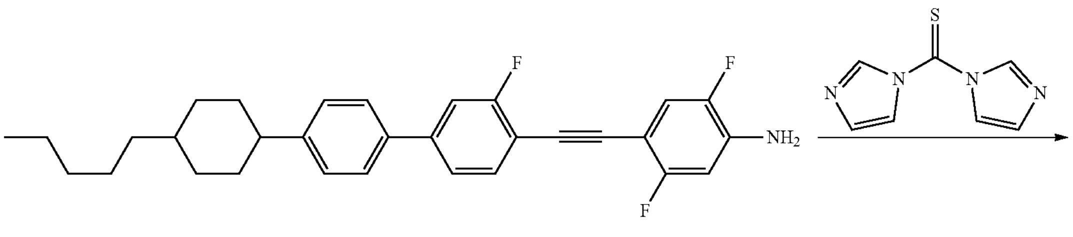

(intermediate 4)

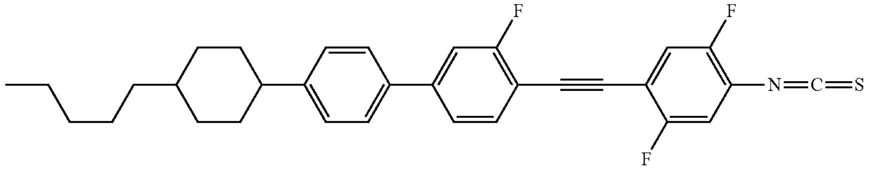

(1-6)

The intermediate 4 (8.9 g), 1,1'-thiocarbonyldiimidazole (10 g), and THF (70 mL) were heated and stirred at 80° C. for 1 hour. The reaction solution was concentrated and purified by silica gel column chromatography (developing liquid:toluene/heptane=2/8 (volume ratio)), and recrystallized from boiling heptane to obtain the compound (1-6): 4-((2,5-difluoro-4-isothiocyanatophenyl)ethynyl)-3-fluoro-4'-(4-pentylcyclohexyl)-1,1'-biphenyl.

The structure of the obtained compound was confirmed by NMR measurement.

$^1$H-NMR (δ ppm: $CDCl_3$): 7.56 (t, 1H), 7.52 (d, 2H), 7.38 (dd, 1H), 7.34-7.29 (m, 4H), 6.94 (dd, 1H), 2.52 (tt, 1H), 1.91 (m, 4H), 1.48 (m, 2H), 1.37-1.20 (m, 9H), 1.07 (m, 2H), 0.90 (t, 3H).

Example 2

Synthesis of a Compound (1-8): 3-fluoro-4-((5-fluoro-4-isothiocyanato-2-methylphenyl)ethynyl)-4'-(4-propylcyclohexyl)-1,1'-biphenyl

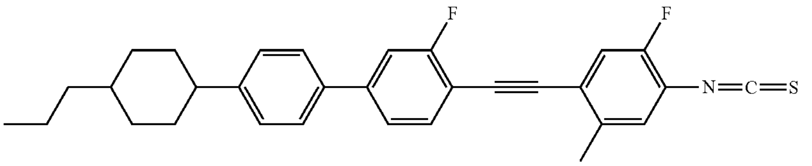 [SMILES: CCCC1CCC(c2ccc(-c3ccc(C#Cc4cc(F)c(N=C=S)cc4C)c(F)c3)cc2)CC1]

A compound represented by Formula (1-8) was synthesized using the same method as the synthesis example described above.

The structure of the obtained compound was confirmed by NMR measurement.

$^1$H-NMR (δ ppm: $CDCl_3$): 7.53 (t, 1H), 7.52 (d, 2H), 7.38 (dd, 1H), 7.34 (dd, 1H), 7.30 (d, 2H), 7.29 (d, 1H), 7.05 (d, 1H), 2.52 (tt, 1H), 2.46 (s, 3H), 1.90 (m, 4H), 1.48 (m, 2H), 1.40-1.20 (m, 5H), 1.07 (m, 2H), 0.91 (t, 3H).

Example 3

Synthesis of a Compound (1-5): 4-((3,5-difluoro-4-isothiocyanatophenyl)ethynyl)-2-fluoro-5-methyl-4'-(4-pentylcyclohexyl)-1,1'-biphenyl

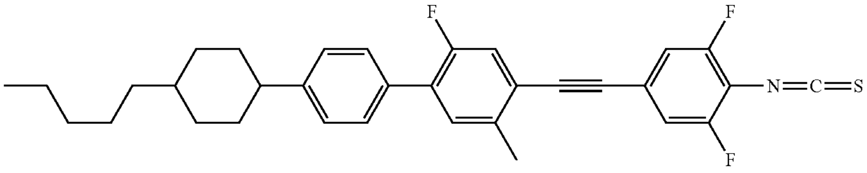 [SMILES: CCCCCC1CCC(c2ccc(-c3cc(C)c(C#Cc4cc(F)c(N=C=S)c(F)c4)cc3F)cc2)CC1]

A compound represented by Formula (1-5) was synthesized using the same method as the synthesis example described above.

The structure of the obtained compound was confirmed by NMR measurement.

$^1$H-NMR (δ ppm: $CDCl_3$): 7.48 (dd, 2H), 7.31-7.28 (m, 3H), 7.24 (d, 1H), 7.12 (d, 2H), 2.51 (tt, 1H), 2.48 (s, 3H), 1.91 (m, 4H), 1.48 (m, 2H), 1.37-1.20 (m, 9H), 1.07 (m, 2H), 0.90 (t, 3H).

Example 4

Synthesis of a Compound (1-10): 1-fluoro-2-((4-isothiocyanatophenyl)ethynyl)-4-methyl-5-((4-(4-pentylcyclohexyl)phenyl)ethynyl)benzene

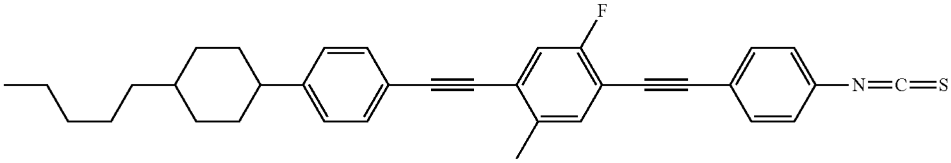 [SMILES: CCCCCC1CCC(c2ccc(C#Cc3cc(F)c(C#Cc4ccc(N=C=S)cc4)cc3C)cc2)CC1]

A compound represented by Formula (1-10) was synthesized using the same method as the synthesis example described above.

The structure of the obtained compound was confirmed by NMR measurement.

$^1$H-NMR (δ ppm: $CDCl_3$): 7.52 (d, 2H), 7.45 (d, 2H), 7.34 (d, 1H), 7.23-7.20 (m, 5H), 2.49 (tt, 1H), 2.45 (s, 3H), 1.89 (m, 4H), 1.45 (m, 2H), 1.36-1.20 (m, 9H), 1.05 (m, 2H), 0.90 (t, 3H).

Compounds in Examples are represented by symbols based on the definitions in Table 2. Numbers in parentheses after the symbols correspond to numbers of the compounds. The symbol (–) means other liquid crystalline compounds. The proportion (percentage) of the liquid crystalline compounds is weight percentage (weight %) based on the weight of the liquid crystal composition. Finally, property values of the composition are summarized.

TABLE 2
| Notation of compounds using symbols $R-(A_1)-Z_1-\ldots-Z_n-(A_n)-R'$ | Symbol |
|---|---|
| 1) Left terminal group R— | |
| $C_nH_{2n+1}$— | n— |
| $C_nH_{2n+1}O$— | nO— |
| $CH_2{=}CH$— | V— |
| $C_nH_{2n+1}$—C≡C— | nT— |
| 2) Right terminal group —R' | |
| —$C_nH_{2n+1}$ | —n |
| —$OC_nH_{2n+1}$ | —On |
| —$CH{=}CH_2$ | —V |
| —C≡C—$C_nH_{2n+1}$ | —Tn |
| —C≡N | —C |
| —C≡C—C≡N | —TC |
| —N=C=S | —NCS |
| —C≡C—$CF_3$ | —TCF3 |
| —$C_nH_{2n}$—$CH{=}CH_2$ | —nV |
| 3) Bonding group —$Z_n$— | |
| —$C_2H_4$— | 2 |
| —COO— | E |
| —CH=CH— | V |
| —C≡C— | T |
| —C≡C—C≡C— | TT |
| 4) Ring structure —$A_n$— | |
| 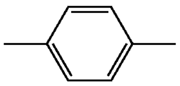 | B |
| 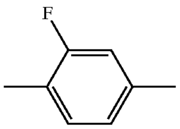 or 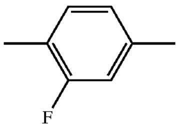 | B(2F) |
| 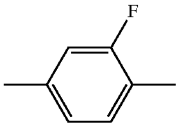 or 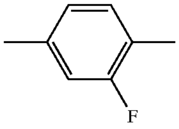 | B(F) |
| 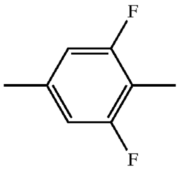 | B(F, F) |
| 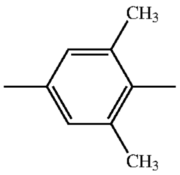 | B(3Me, 5Me) |
| 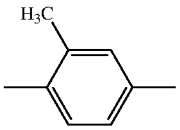 or 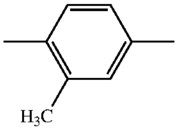 | B(2Me) |

TABLE 2-continued
Notation of compounds using symbols
$R-(A_1)-Z_1-\ldots-Z_n-(A_n)-R'$
| | Symbol |
|---|---|
| 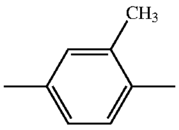 or 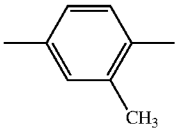 | B(Me) |
| 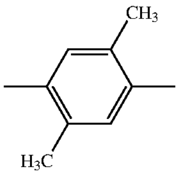 or 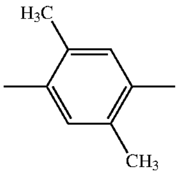 | B(2Me, 5Me) |
| 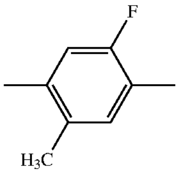 or 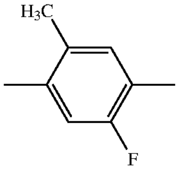 | B(2Me, 5F) |
| 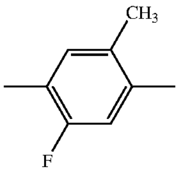 or 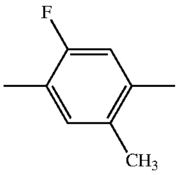 | B(2F, 5Me) |
5) Notation example
Example No. 1 3—HBB(F)TB(2Me,5F)—NCS
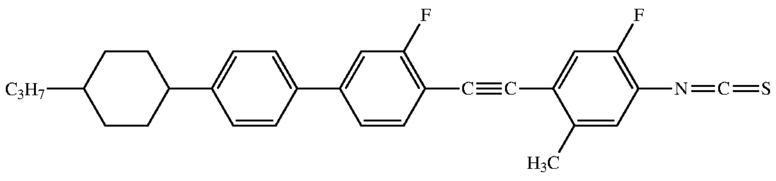
Example No. 2: 3—BTB(2Me)—NCS
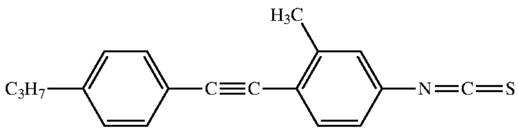
Example No. 3 3—BB(F)TB(Me)—NCS
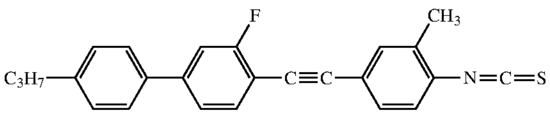

[Comparative Example 1] Liquid Crystal Composition C1

| | | |
|---|---|---|
| 3-BTB(2Me)-NCS | (2-5) | 20% |
| 4-BTB(2Me)-NCS | (2-5) | 10% |
| 5-BTB(2Me)-NCS | (2-5) | 15% |
| 3-BB(F)TB(2Me,5F)-NCS | (3-5) | 10% |
| 3-BB(F)TB(Me)-NCS | (3-9) | 13% |
| 5-BB(F)TB(Me)-NCS | (3-9) | 12% |
| 3-BB(F)B(F,F)-NCS | (—) | 10% |
| 3-BTB(2Me,5F)TB-NCS | (—) | 10% |
| NI = 101.2° C.; Tc < −40° C.; Δn = 0.471; Δε = 14.6 | | |

The dielectric anisotropy (Δε@28 GHz) and the dielectric loss tangent (tan δ@28 GHz) of the liquid crystal composition C1 at 28 GHz were as follows.

$$\Delta\varepsilon@28\ \text{GHz} = 1.27$$

$$\tan\delta@28\ \text{GHz} = 0.006$$

[Example 5] Liquid Crystal Composition M1

| | | |
|---|---|---|
| 5-HBB(F)TB(2F,5F)-NCS | (1-6) | 10% |
| 3-BTB(2Me)-NCS | (2-5) | 15% |
| 5-BTB(2Me)-NCS | (2-5) | 12% |
| 3-BB(F)TB(2Me,5F)-NCS | (3-5) | 15% |
| 3-BB(F)TB(Me)-NCS | (3-9) | 10% |
| 5-BB(F)TB(Me)-NCS | (3-9) | 10% |
| 3-BB(F)B(F,F)-NCS | (—) | 18% |
| 3-BTB(2Me,5F)TB-NCS | (—) | 10% |
| NI = 155.1°C; Tc < −40° C.; Δn = 0.509; Δε = 15.7 | | |

The dielectric anisotropy (Δε@28 GHz) and the dielectric loss tangent (tan δ@28 GHz) of the liquid crystal composition M1 at 28 GHz were as follows.

$$\Delta\varepsilon@28\ \text{GHz} = 1.32$$

$$\tan\delta@28\ \text{GHz} = 0.006$$

The compound (1) was added to Comparative Example 1, and a composition composed of the compound (1) to the compound (3) corresponds to Example 5. Herein, while Δε@28 GHz of the composition of Comparative Example 1 was 1.27, Δε@28 GHz of the composition of Example 5 was 1.32, which may be said to be large. tan δ@28 GHz was 0.006 respectively, and was small in both cases. The upper limit temperature of Comparative Example 1 was 101.2° C. and the lower limit temperature was <−40° C., while the upper limit temperature of Example 5 was 155.1° C. and the lower limit temperature was <−40° C. It has been confirmed that applying the compound (1) can obtain a liquid crystal composition having a nematic phase in a wider temperature range.

[Example 6] Liquid Crystal Composition M2

| | | |
|---|---|---|
| 3-HBB(F)TB(2Me,5F)-NCS | (1-8) | 10% |
| 3-BTB(2Me)-NCS | (2-5) | 15% |
| 5-BTB(2Me)-NCS | (2-5) | 12% |
| 3-BB(F)TB(2Me,5F)-NCS | (3-5) | 15% |
| 3-BB(F)TB(Me)-NCS | (3-9) | 10% |
| 5-BB(F)TB(Me)-NCS | (3-9) | 10% |
| 3-BB(F)B(F,F)-NCS | (——) | 18% |
| 3-BTB(2Me,5F)TB-NCS | (——) | 10% |
| NI = 154.2° C.; Tc < −30° C.; Δn = 0.506; Δε = 15.9 | | |

The dielectric anisotropy (Δε@28 GHz) and the dielectric loss tangent (tan δ@28 GHz) of the liquid crystal composition M2 at 28 GHz were as follows.

$$\Delta\varepsilon@28\ \text{GHz} = 1.32$$

$$\tan\delta@28\ \text{GHz} = 0.007$$

[Example 7] Liquid Crystal Composition M3

| | | |
|---|---|---|
| 5-HBB(2F,5Me)TB(F,F)-NCS | (1-5) | 10% |
| 3-BTB(2Me)-NCS | (2-5) | 15% |
| 5-BTB(2Me)-NCS | (2-5) | 12% |
| 3-BB(F)TB(2Me,5F)-NCS | (3-5) | 15% |
| 3-BB(F)TB(Me)-NCS | (3-9) | 10% |
| 5-BB(F)TB(Me)-NCS | (3-9) | 10% |
| 3-BB(F)B(F,F)-NCS | (—) | 18% |
| 3-BTB(2Me,5F)TB-NCS | (—) | 10% |
| NI = 147.5° C.; Tc < −30° C.; Δn = 0.494; Δε = 15.8 | | |

The dielectric anisotropy (Δε@28 GHz) and the dielectric loss tangent (tan δ@28 GHz) of the liquid crystal composition M3 at 28 GHz were as follows.

$$\Delta\varepsilon@28\ \text{GHz} = 1.30$$

$$\tan\delta@28\ \text{GHz} = 0.006$$

[Example 8] Liquid Crystal Composition M4

| | | |
|---|---|---|
| 3-HBB(F)TB(2Me,5F)-NCS | (1-8) | 10% |
| 3-BTB(2Me)-NCS | (2-5) | 20% |
| 4-BTB(2Me)-NCS | (2-5) | 10% |
| 5-BTB(2Me)-NCS | (2-5) | 15% |
| 3-BB(F)TB(2Me,5F)-NCS | (3-5) | 10% |
| 3-BB(F)TB(Me)-NCS | (3-9) | 8% |
| 5-BB(F)TB(Me)-NCS | (3-9) | 7% |
| 3-BTB(2Me,5F)TB-NCS | (—) | 10% |
| 5-BB(F)TB(2Me)B(3Me,5Me)-NCS | (—) | 10% |
| NI = 125.1° C.; Tc < −40° C.; Δn = 0.478; Δε = 12.6 | | |

The dielectric anisotropy (Δε@28 GHz) and the dielectric loss tangent (tan δ@28 GHz) of the liquid crystal composition M4 at 28 GHz were as follows.

$$\Delta\varepsilon@28\ \text{GHz} = 1.28$$

$$\tan\delta@28\ \text{GHz} = 0.006$$

[Example 9] Liquid Crystal Composition M5

| | | |
|---|---|---|
| 5-HBTB(2Me,5F)TB-NCS | (1-10) | 10% |
| 3-BTB(2Me)-NCS | (2-5) | 20% |
| 4-BTB(2Me)-NCS | (2-5) | 10% |
| 5-BTB(2Me)-NCS | (2-5) | 15% |
| 3-BB(F)TB(2Me,5F)-NCS | (3-5) | 10% |
| 3-BB(F)TB(Me)-NCS | (3-9) | 13% |
| 5-BB(F)TB(Me)-NCS | (3-9) | 12% |
| 3-BTB(2Me,5F)TB-NCS | (—) | 10% |
| NI = 120.0° C.; Tc < −40° C.; Δn = 0.485; Δε = 11.9 | | |

The dielectric anisotropy (Δε@28 GHz) and the dielectric loss tangent (tan δ@28 GHz) of the liquid crystal composition M5 at 28 GHz were as follows.

$$\Delta\varepsilon@28\ \text{GHz} = 1.23$$

$$\tan\delta@28\ \text{GHz} = 0.006$$

[Example 10] Liquid Crystal Composition M6

| | | |
|---|---|---|
| 5-HBB(2Me,5F)TB(F,F)-NCS | (1-5) | 10% |
| 4-BTB(F,F)-NCS | (2-2) | 7% |
| 3-BTB(2Me)-NCS | (2-5) | 10% |
| 5-BTB(2Me)-NCS | (2-5) | 10% |
| 3-BB(F)TB(2Me,5F)-NCS | (3-5) | 15% |
| 3-BB(F)TB(Me)-NCS | (3-9) | 10% |
| 5-BB(F)TB(Me)-NCS | (3-9) | 10% |
| 3-BB(F)B(F,F)-NCS | (—) | 18% |
| 3-BTB(2Me,5F)TB-NCS | (—) | 10% |
| NI = 148.1° C.; Tc < −30° C.; Δn = 0.488; Δε = 16.8 | | |

The dielectric anisotropy (Δε@28 GHz) and the dielectric loss tangent (tan δ@28 GHz) of the liquid crystal composition M6 at 28 GHz were as follows.

$$\Delta\varepsilon@28\ \text{GHz} = 1.31$$

$$\tan\delta@28\ \text{GHz} = 0.007$$

[Example 11] Liquid Crystal Composition M7

| | | |
|---|---|---|
| 5-HBB(2Me,5F)TB(F,F)-NCS | (1-5) | 10% |
| 3-BTB(2Me)-NCS | (2-5) | 10% |
| 5-BTB(2Me)-NCS | (2-5) | 10% |
| 3-BTB(Me)-NCS | (2-6) | 7% |
| 3-BB(F)TB(2Me,5F)-NCS | (3-5) | 15% |
| 3-BB(F)TB(Me)-NCS | (3-9) | 10% |

-continued

| | | |
|---|---|---|
| 5-BB(F)TB(Me)-NCS | (3-9) | 10% |
| 3-BB(F)B(F,F)-NCS | (—) | 18% |
| 3-BTB(2Me,5F)TB-NCS | (—) | 10% |
| NI = 145.6° C.; Tc < −30° C.; Δn = 0.490; Δε = 16.1 | | |

The dielectric anisotropy (Δε@28 GHz) and the dielectric loss tangent (tan δ@28 GHz) of the liquid crystal composition M7 at 28 GHz were as follows.

$$\Delta\varepsilon@28\ \text{GHz} = 1.34$$

$$\tan\delta@28\ \text{GHz} = 0.006$$

The compositions of Example 5 to Example 11 each contain the compound (1) to the compound (3). Retaining the basic performance as a liquid crystal composition, the liquid crystal compositions containing the compound (1) to the compound (3) were capable of reducing the value of tan δ@28 GHz while maintaining a large Δε@28 GHz. In particular, the liquid crystal composition containing the compound (1) has a very high upper limit temperature while maintaining a low lower limit temperature.

The properties required for a liquid crystal composition include: a large dielectric anisotropy (Δε) that enables large phase control in a frequency domain used for phase control; and a small dielectric loss tangent (tan δ) proportional to absorption energy of electromagnetic wave signals of the liquid crystal composition. The results of Examples and Comparative Example have illustrated that the composition of the disclosure has a large dielectric anisotropy (Δε@28 GHz) and a small dielectric loss tangent (tan δ@28 GHz). In general, the smaller tan δ is, the lower absorption energy of electromagnetic waves becomes. Accordingly, the liquid crystal composition using the compound represented by Formula (1) is capable of reducing the absorption energy of electromagnetic wave signals and can set the loss of electromagnetic wave signals to be smaller. Based on the above, it can be concluded that the liquid crystal composition of the disclosure can perform transmission of electromagnetic wave signals more efficiently.

INDUSTRIAL APPLICABILITY

The disclosure is capable of providing a liquid crystalline compound that satisfies at least one of physical properties of the compound, such as stability against heat, a high clearing point, a very large refractive index anisotropy, and excellent compatibility with other liquid crystalline compounds. The composition containing the compound of the disclosure is capable of satisfying at least one of properties of the composition, such as a large dielectric anisotropy (large refractive index anisotropy) in a frequency domain for electromagnetic wave control, a small dielectric loss tangent (tan δ), and a large dielectric anisotropy at low frequencies for reduction of driving voltage, while having a high upper limit temperature of a nematic phase and a low lower limit temperature of the nematic phase. Furthermore, it becomes possible to further satisfy at least one of properties of the composition, such as a liquid crystal composition having a small viscosity, a large specific resistance in a driving frequency domain, and stability against heat, to provide a more preferable liquid crystal composition. Elements containing this composition may be used for control of electromagnetic wave signals having frequencies in a range from 1 GHz to 10 THz.

What is claimed is:

1. A liquid crystalline compound, represented by Formula (1), (1)

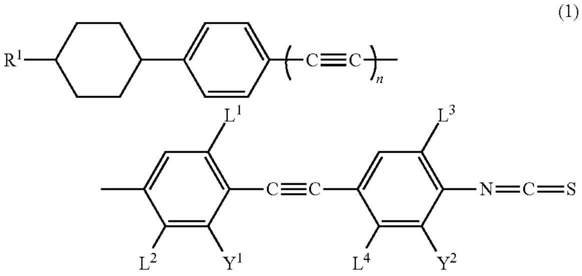

wherein in Formula (1), $R^1$ is hydrogen, halogen, or alkyl having 1 to 12 carbon atoms, wherein, in the alkyl, at least one $—CH_2—$ may be substituted with —O— or —S—, at least one $—(CH_2)_2—$ may be substituted with —CH═CH— or —C≡C—, wherein at least one hydrogen in the alkyl may be substituted with halogen;

$L^1$, $L^2$, $L^3$, and $L^4$ are hydrogen, fluorine, chlorine, methyl, or ethyl;

$Y^1$ and $Y^2$ are hydrogen, fluorine, or chlorine; and n is 0 or 1, with the proviso that when n is 0, $L^1$, $L^2$, $L^3$, and $L^4$ are not selected such that any two of $L^1$, $L^2$, $L^3$, and $L^4$ are methyl and the remaining two are hydrogen, fluorine, chlorine, or ethyl.

2. The liquid crystalline compound according to claim 1, wherein the compound represented by Formula (1) is represented by any one of Formula (1-1) to Formula (1-18), (1-1)

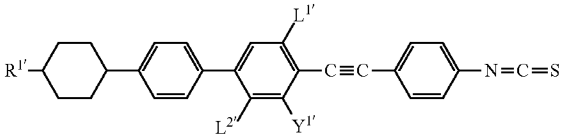

(1-2)

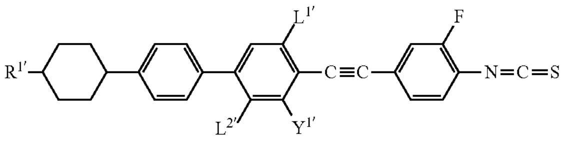

(1-3)

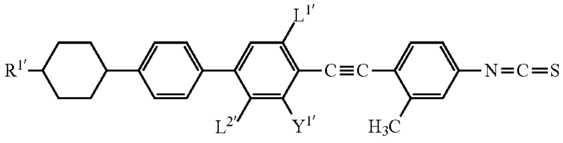

(1-4)

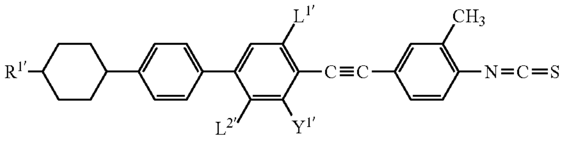

-continued (1-5)

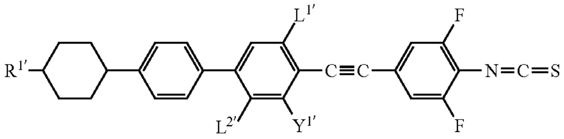

(1-6)

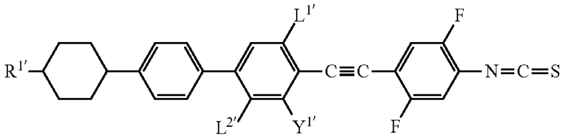

(1-7)

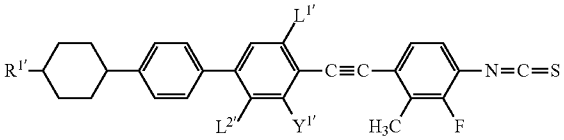

(1-8)

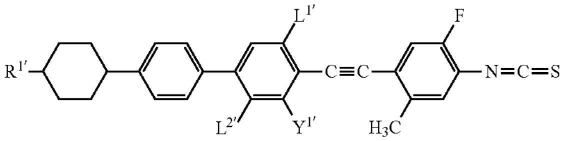

(1-9)

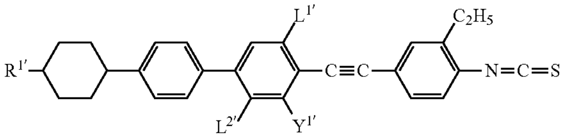

(1-10)

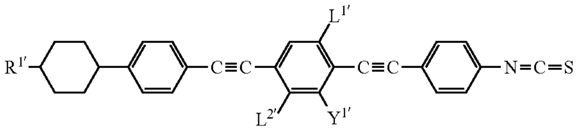

(1-11)

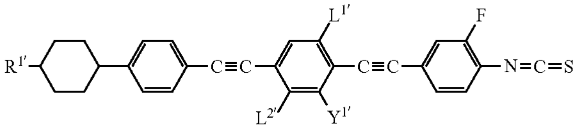

(1-12)

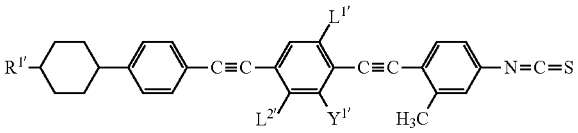

(1-13)

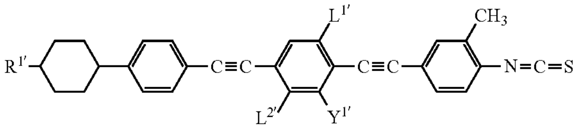

-continued (1-14)

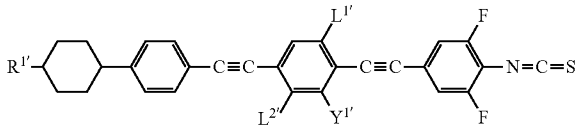

(1-15)

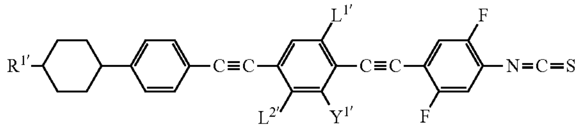

(1-16)

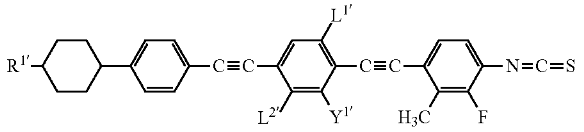

(1-17)

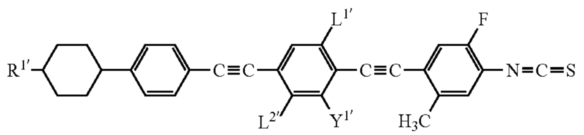

(1-18)

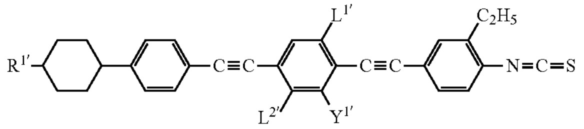

in Formula (1-1) to Formula (1-18), $R^{1'}$ is alkyl having 1 to 12 carbon atoms, wherein, in the alkyl, at least one —$CH_2$— may be substituted with —O— or —S—, at least one —$(CH_2)_2$— may be substituted with —CH═CH— or —C≡C—, wherein at least one hydrogen in the alkyl may be substituted with halogen;

$L^{1'}$ is fluorine or methyl, and $L^{2'}$ is hydrogen, fluorine, or methyl; and $Y^{1'}$ is hydrogen or fluorine, with the proviso that in Formula (1-1) Formula (1-2), Formula (1-5), Formula (1-6), and Formula (1-9), $L^{1'}$ and $L^{2'}$ are not simultaneously methyl; and with the proviso that in Formula (1-3), Formula (1-4), Formula (1-7), and Formula (1-8), $L^{1'}$ and $L^{2'}$ are not selected such that only one of $L^{1'}$ and $L^{2'}$ is methyl.

3. A liquid crystal composition comprising at least one liquid crystalline compound according to claim 1.

4. The liquid crystal composition according to claim 3, further comprising at least one compound selected from compounds represented by Formula (2) and Formula (3), (2)

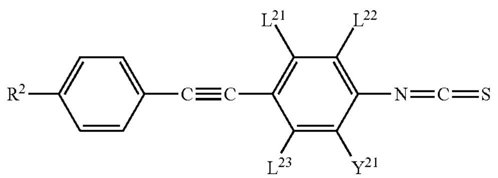

-continued (3)

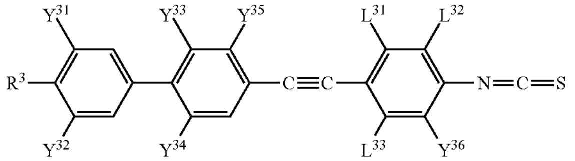

wherein in Formula (2) and Formula (3), $R^2$ and $R^3$ are hydrogen, halogen, or linear alkyl having 1 to 12 carbon atoms, wherein, in the linear alkyl, at least one —$CH_2$— may be substituted with —O— or —S—, at least one —$(CH_2)_2$— may be substituted with —CH═CH— or —C≡C—, wherein at least one hydrogen in the linear alkyl may be substituted with halogen;

$L^{21}$, $L^{22}$, $L^{23}$, $L^{31}$, $L^{32}$, and $L^{33}$ are hydrogen, halogen, alkyl having 1 to 3 carbon atoms, fluorinated alkyl having 1 to 3 carbon atoms, or cycloalkyl having 3 to 5 carbon atoms; and $Y^{21}$, $Y^{31}$, $Y^{32}$, $Y^{33}$, $Y^{34}$, $Y^{35}$ and $Y^{36}$ are hydrogen or halogen.

5. The liquid crystal composition according to claim 4, comprising at least one compound selected from the group of compounds represented by Formula (2-1) to Formula (2-10) as the compound represented by Formula (2), (2-1)

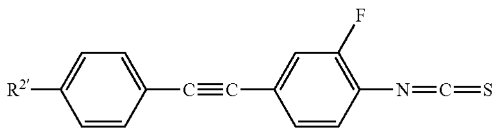

(2-2)

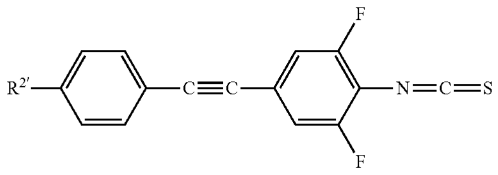

(2-3)

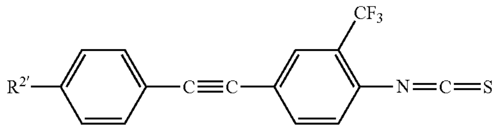

(2-4)

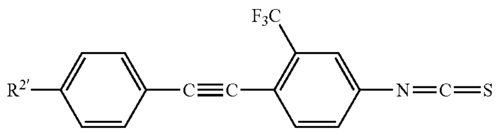

(2-5)

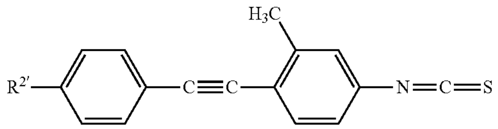

(2-6)

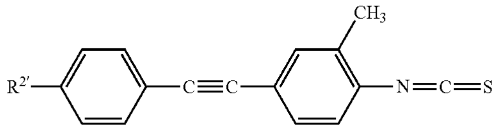

-continued (2-7)

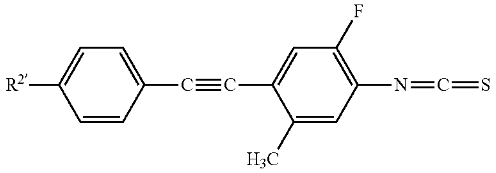

(2-8)

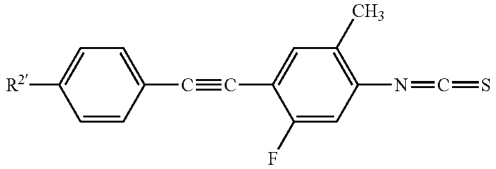

(2-9)

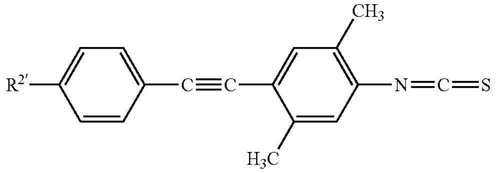

(2-10)

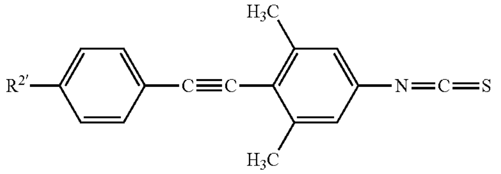

wherein in Formula (2-1) to Formula (2-10), $R^{2'}$ is linear alkyl having 1 to 12 carbon atoms, wherein, in the linear alkyl, at least one $-(CH_2)_2-$ may be substituted with $-CH{=}CH-$ or $-C{\equiv}C-$.

6. The liquid crystal composition according to claim 4, comprising at least one compound selected from the group of compounds represented by Formula (3-1) to Formula (3-11) as the compound represented by Formula (3), (3-1)

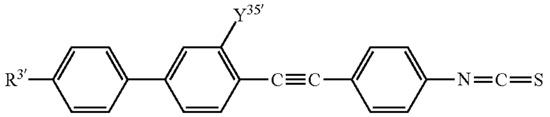

(3-2)

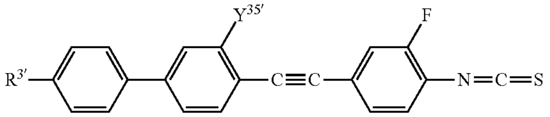

(3-3)

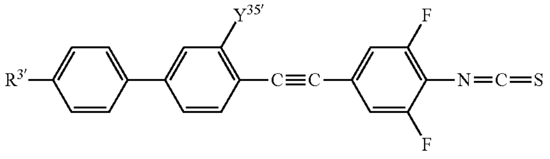

-continued (3-4)

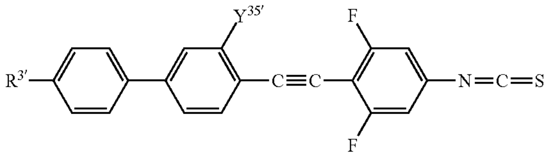

(3-5)

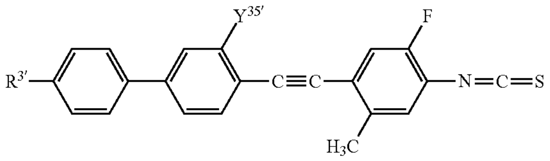

(3-6)

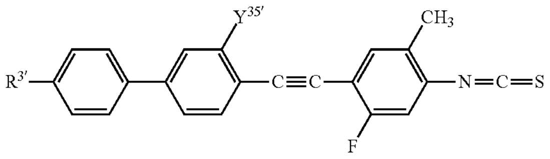

(3-7)

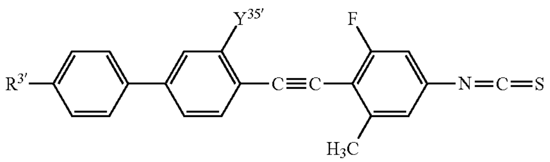

(3-8)

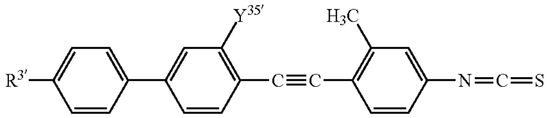

(3-9)

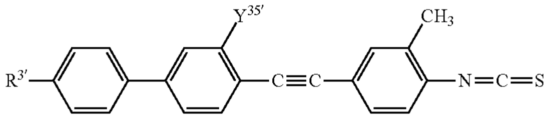

(3-10)

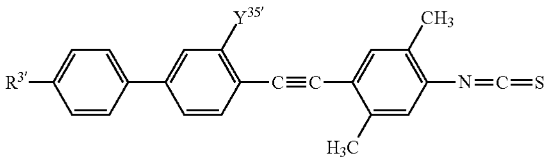

(3-11)

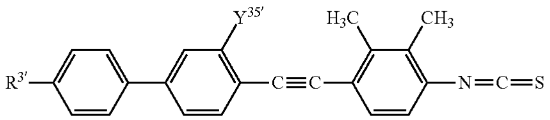

wherein in Formula (3-1) to Formula (3-11), $R^{3'}$ is linear alkyl having 1 to 12 carbon atoms, wherein in the linear alkyl, at least one $-(CH_2)_2-$ may be substituted with $-CH{=}CH-$ or $-C{\equiv}C-$; and $Y^{35'}$ is hydrogen, fluorine, or chlorine.

7. The liquid crystal composition according to claim 4, wherein based on a weight of the liquid crystal composition, a proportion of the compound represented by Formula (1) is in a range from 5 weight % to 25 weight %, and a proportion of the compound represented by Formula (2) is in a range from 10 weight % to 55 weight %.

8. The liquid crystal composition according to claim 4, wherein based on a weight of the liquid crystal composition, a proportion of the compound represented by Formula (1) is in a range from 5 weight % to 25 weight %, and a proportion of the compound represented by Formula (3) is in a range from 20 weight % to 50 weight %.

9. The liquid crystal composition according to claim 4, wherein based on a weight of the liquid crystal composition, a proportion of the compound represented by Formula (1) is in a range from 5 weight % to 25 weight %, a proportion of the compound represented by Formula (2) is in a range from 10 weight % to 55 weight %, and a proportion of the compound represented by Formula (3) is in a range from 20 weight % to 50 weight %.

10. The liquid crystal composition according to claim 3, having a refractive index anisotropy at 25° C. at a wavelength of 589 nm of 0.40 or more.

11. The liquid crystal composition according to claim 3, having a dielectric anisotropy at 25° C. at a frequency of 1 kHz of 10 or more.

12. The liquid crystal composition according to claim 3, having a dielectric anisotropy of 1.0 to 3.0 at 25° C. in at least one frequency range from 1 GHz to 10 THz.

13. The liquid crystal composition according to claim 3, further comprising an optically active compound.

14. The liquid crystal composition according to claim 3, further comprising a polymerizable compound.

15. The liquid crystal composition according to claim 3, further comprising at least one of an antioxidant, an ultraviolet absorber, an antistatic agent, and a dichroic dye.

16. An element comprising the liquid crystal composition according to claim 3, the element being used for switching and capable of reversibly controlling a dielectric constant by reversibly changing an orientation direction of liquid crystal molecules.

17. An element comprising the liquid crystal composition according to claim 3 and used for electromagnetic wave control in a frequency range from 1 GHz to 10 THz.

18. A liquid crystal lens comprising the liquid crystal composition according to claim 3.

19. A birefringent lens for stereoscopic image display comprising the liquid crystal composition according to claim 3.

20. A light modulator comprising the liquid crystal composition according to claim 3.

* * * * *